US009631001B2

(12) United States Patent
Gilles et al.

(10) Patent No.: US 9,631,001 B2

(45) Date of Patent: Apr. 25, 2017

(54) PEPTIDE ANTAGONISTS OF THE VASOPRESSIN-2 RECEPTOR

(71) Applicants: COMMISSARIAT A L'ENERGIE ATOMIQUE ET AUX ENERGIES ALTERNATIVES, Paris (FR); Centre National de la Recherche Scientifique (CNRS), Paris (FR); Institut National De La Sante Et De La Recherche Medicale (INSERM), Paris (FR); University of Regensburg, Regensburg (DE); Universite De Liege, Liege (BE)

(72) Inventors: Nicolas Gilles, Mitry-Mory (FR); Denis Servent, Versailles (FR); Loïc Quinton, Stree-Lez-Huy (BE); Helen Reinfrank, Kofering (DE); Ralph Witzgall, Regensburg (DE); Bernard Mouillac, Montpellier (FR); Christiane Mendre, Argelliers (FR)

(73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR); UNIVERSITY OF REGENSBURG, Regensberg (DE); UNIVERSITY DE LIEGE, Liege (BE)

( * ) Notice: Subject to any disclaimer, the term of this patent is extended or adjusted under 35 U.S.C. 154(b) by 0 days.

(21) Appl. No.: 14/427,733

(22) PCT Filed: Sep. 17, 2013

(86) PCT No.: PCT/IB2013/058615

§ 371 (c)(1),
(2) Date: Mar. 12, 2015

(87) PCT Pub. No.: WO2014/041526

PCT Pub. Date: Mar. 20, 2014

(65) Prior Publication Data

US 2015/0252086 A1 Sep. 10, 2015

(30) Foreign Application Priority Data

Sep. 17, 2012 (EP) .................................... 12306120

(51) Int. Cl.

| | |
|---|---|
| ***C07K 14/46*** | (2006.01) |
| ***A61K 38/17*** | (2006.01) |
| *A61K 38/00* | (2006.01) |

(52) U.S. Cl.

CPC .......... *C07K 14/46* (2013.01); *A61K 38/1703* (2013.01); *A61K 38/00* (2013.01)

(58) Field of Classification Search

None

See application file for complete search history.

(56) References Cited

U.S. PATENT DOCUMENTS 5,663,143 A 9/1997 Ley et al.
2008/0234183 A1 9/2008 Hallbrink et al.

FOREIGN PATENT DOCUMENTS

WO WO 2007/019267 A1 2/2007

OTHER PUBLICATIONS

Zucker et al. (Oncogene 2000, 19, 6642-6650).*

International Search Report and Written Opinion from International Application No. PCT/IB2013/058615 mailed Feb. 5, 2014.

"RecName: Full=Dendrotoxin-B; AltName: Full=Venom basic protease inhibitor B;", XP002690782, retrieved from EBI accession No. UNIPROT:P00983, Database Accession No. P00983; abstract; sequence; Jul. 21, 1986.

Strydom D Jet al.; "The Amino Acid Sequence of a Weak Trypsin Inhibitor B from Dendroaspis Polylepis Polylepis (Black Mamba) Venom//Aminosaeuesequenz Des Schwachen Trypsininhibitirs B Aus Dem Gift Von Dendroaspis Polylepis Polylepis (Schwarze Mamba)"; *Hoppe-Seyler's Zeitschrift Fuer Physiologische Chemie, Walter de Gruyter*, Berlin, DE; vol. 362, No. 10; Oct. 1, 1981; pp. 1377-1384; XP001094581.

Inagaki, Hidetoshi et al.; "Functional Characterization of Kunitz-Type Protease Inhibitormulgins Identified from New Guinean Pseudoechis Asutralis"; *Toxicon*; vol. 59, No. 1; Oct. 7, 2011; pp. 74-80; XP028437775.

"RecName: Full=Protease Imhibitor Mulgin-1; Flags: Precursor;", XP002690783; retrieved from EBI accession No. UNIPORT:Q6ITC1; Database accession No. Q6ITC1 sequence.

Veeraveedu P T et al.; "Arginine Vasopressin Receptor Antagonists (vaptans): Pharmacological Tools and Potential Therapeutic Agents"; *Drug Discovery Today*; vol. 15, No. 19-20; Oct. 1, 2010; pp. 826-841; XP027400361.

* cited by examiner

*Primary Examiner* — James H Alstrum Acevedo
*Assistant Examiner* — Tara Martinez
(74) *Attorney, Agent, or Firm* — Alston & Bird LLP

(57) ABSTRACT

The invention relates to a new group of snake venom basic protease inhibitors having vasopressin-2 receptor antagonist activity that can be used in therapy, diagnosis, medical imaging, drug screening and research.

13 Claims, 16 Drawing Sheets

A

```
                                                                                          % identity with
                                                                                            SEQ ID NO: 1

U-Da2a     (SEQ ID NO: 1)     RPSFCNLPVKPGPCNGFFSAFYYSQKTNKCHSFTYGGCKGNANRFSTIEKCRRTCVG      100
DTx-B/A27  (SEQ ID NO: 2)     RPYACELIVAAGPCMFFISAFYYSKGANKCYPFTYSGCRGNANRFKTIEECRRTCVV       67
Dtx-E/H55  (SEQ ID NO: 6)   LQHRTFCKLPAEPGPCKASIPAFYYNWAAKKCQLFHYGGCKGNANRFSTIEKCRHACVG       63
Mulgin-1   (SEQ ID NO: 4)   KDRPRFCELPADPGPCNGLFQAFYYNPVQRKCLKFRYGGCKGNPNTFKTIEECKRTCAA       61
Blackel-3  (SEQ ID NO: 5)   KDRPKFCELPADPGPCNGLFQAFYYNPVQRKCLKFRYGGCKANPNTFKTIEECKRICAA       60
Dtx-K      (SEQ ID NO: 8)     AAKYCKLPLRIGPCKRKIPSFYYKWKAKQCLPFDYSGCGGNANRFKTIEECRRTCVG       54
Alpha-Dtx  (SEQ ID NO: 9)   QPRRKLCILHRNPGRCYDKIPAFYYNQKKKQCERFDWSGCGGNSNRFKTIEECRRTCIG       53
BPTI       (SEQ ID NO: 10)    RPDFCLEPPYTGPCKARIIRYFYNAKAGLCQTFVYGGCRAKRNNFKSAEDCMRTCGGA      42
```

B

```
U-Da2a      1    RPSFCNLPVKPGPCNGFFSAFYYSQKTNKCHSFTYGGCKGNANRFSTIEKCRRTCVG  57
                 RP FC LP  PGPCNG F AFYY     KC  F YGGCK N N F TIE C R C
Blackel 3   27   RPKFCELPADPGPCNGLFQAFYYNPVQRKCLKFRYGGCKANPNTFKTIEECKRICAA  83

                 Identities = 34/57 (60%), Gaps = 0/57 (0%)
```

FIGURE 1

A
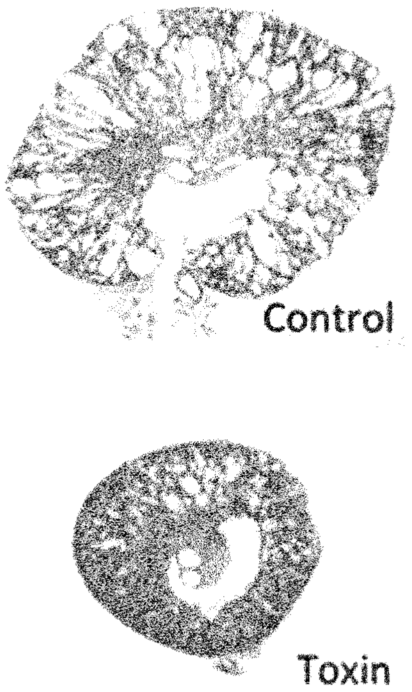
B
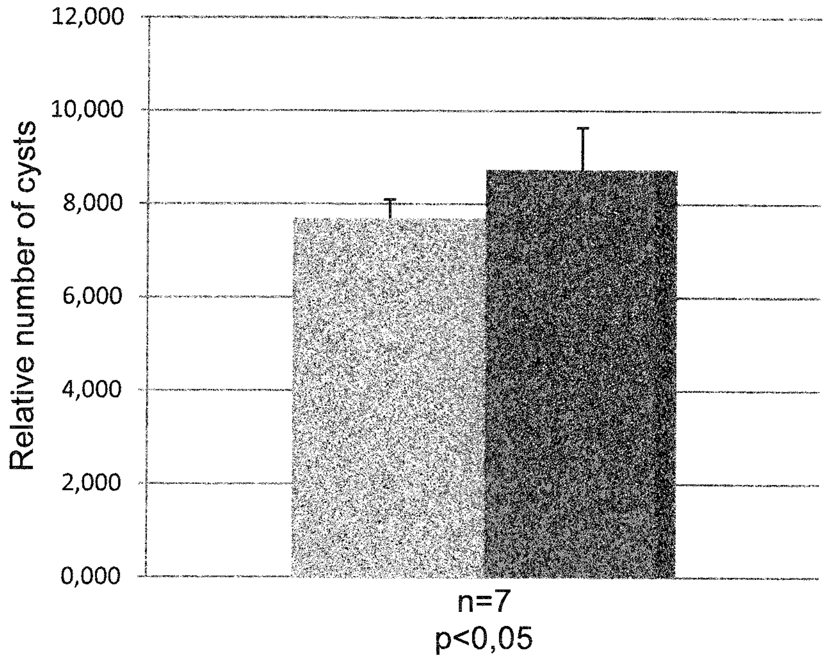
FIGURE 13

PEPTIDE ANTAGONISTS OF THE VASOPRESSIN-2 RECEPTOR

FIELD

The present invention relates to a new group of snake venom basic protease inhibitors having vasopressin-2 receptor antagonist activity that can be used in therapy, diagnosis, medical imaging, drug screening and research.

BACKGROUND

G protein-coupled-receptors (GPCRs) constitute the largest family of integral membrane proteins. More than 800 GPCRs have been identified, the underlying genes represent 2 to 3% of the coding sequences in the human genome. They participate in the regulation of most physiological functions and are the targets of approximately 30% of currently marketed drugs. Among GPCRs, the arginine-vasopressin V2 receptor subtype (also known as vasopressin-2, vasopressin 2, vasopressin type 2 or V2 receptor and abbreviated AVPR2 or V2R) is considered as a prototype of receptors coupled to the intracellular cyclic adenosine monophosphate (cAMP) signalling pathway. It represents a fundamental and therapeutic model.

Arginine-vasopressin (AVP), also known as anti-diuretic hormone, is a 9-amino acid cyclic peptide produced in the hypothalamus. It exerts its action via 3 distinct receptor subtypes: vasopressin 1a (V1aR), vasopressin 1b (V1bR) and vasopressin 2 (V2R). The actions of V1aR and V1bR are mediated via their interaction with the G protein Gq leading to an increase in intracellular calcium concentration. The V1aR is mainly expressed in the liver, smooth muscle cells (vasoconstriction), platelets, brain, retina and reproductive organs, whereas the V1bR is mainly expressed in the anterior pituitary gland where its stimulation controls the corticotropic axis in response to stress. V1bR is also expressed in the pancreas and adrenal glands where it regulates the secretion of glucagon, insulin and catecholamines. The V2R is located in the renal collecting duct where it is coupled to the Gs protein. Gs activate adenylate cyclase which in turn leads to an increased cyclic AMP production. cAMP activates protein kinase A which phosphorylates and activates water channels called aquaporins responsible for water reabsorption in the kidney. The V2R is also expressed in the inner ear where it regulates its osmotic pressure.

V2R participates in the regulation of major physiological functions and is a target for the development of new therapeutic drugs for treating various pathologies. Non-peptidic V2R antagonists, named vaptans, have been developed and tested in numerous clinical trials but most of them were not approved by the drug authorizing authorities because of their hepatotoxicity. Today, Tolvaptan (OPC-41061) and Conivaptan (YM-087) only, have been approved by the FDA, and/or EMEA.

Pathological Conditions Characterized by Euvolemic or Hypervolemic Hyponatremia

The excess secretion of AVP is a key etiologic factor for diseases such as hyponatremia and explains why the use of V2R antagonists is so efficient in pathological conditions characterized by euvolemic or hypervolemic hyponatremia, such as SIADH (Syndrome of Inappropriate AntiDiuretic Hormone secretion), hepatic cirrhosis and congestive heart failure (CHF; Ghali et al., Cardiology, 2008, 111, 147-157). SIADH is caused by the hypersecretion of AVP which leads to excessive water retention and consequently a decrease in $Na^+$ concentration and edema in the lung and central nervous system. By their diuretic effect V2R antagonists increase or normalize serum $Na^+$ levels. Tolvaptan (OPC-41061) and Conivaptan (YM-087) have been approved by the FDA, and/or EMEA on patients diagnosed with euvolemic and hypervolemic hyponatremia, SIADH, congestive heart failure and cirrhosis (Arai et al., Curr Opin Pharmacol., 2007, 7, 124-129; Manning et al., Prog. Brain Res., 2008, 170, 473-412). V2R antagonists could be potentially beneficial in other pathological conditions characterized by euvolemic or hypervolemic hyponatremia, such as cerebral oedema (Walcott et al., Neurotherapeutics, 2012, 9, 65-72).

Nephrogenic Syndrome of Inappropriate Antidiuresis (NSIAD)

The NSIAD is due to V2R mutations such as R137C and R137L which are responsible for a constitutive activity of the receptor. Patients present hyponatremia and a high urinary osmolality despite low serum vasopressin levels. The V2R antagonists Satavaptan and Tolvaptan, either in cell cultures (Tenenbaum et al., PLoS One, 2009, 4, e8333) or in patients with NSIAD (Decaux et al., JASN, 2007, 18, 606-612) are unable to inhibit this constitutive activity.

Congenital Nephrogenic Diabetes Insipidus (cNDI)

This disease is associated with inactivating mutations of the V2R. Deficient receptors are sequestered inside the cell and cannot be reached by circulating AVP. This leads to polyuria with severe dehydration in particular in children. The V2R antagonists (vaptans) behave as pharmacochaperones, they are able to penetrate the cell and can rescue the mutant receptors (Morello et al., J. Clin. Investigation, 2000, 105, 887-895). In some cases this allows the receptor to be stimulated by AVP in order to restore the antidiuretic effect (Bernier et al., J. Am. Soc. Nephrol., 2006, 17, 232-243; Robben et al., Am. J. Physiol. Renal. Physiol., 2007, 292, 253-260). Vaptans were tested in clinical trials but most of them were not approved by the FDA because of their hepatotoxicity (Manning et al., Prog. Brain Res., 2008, 170, 473-512). Today, Tolvaptan only, has been approved by the FDA.

Polycystic Kidney Disease

Polycystic kidney disease is characterized by the appearance of numerous cysts which ultimately lead to end-stage renal failure in the majority of patients. Patients with mutations in the PKD1 and PKD2 genes are unable to concentrate urine despite having a high vasopressin concentration in the blood. The current available treatments for this pathology are dialysis or transplantation. V2R antagonists were shown to slow down the course of the disease in different animal models of recessive and dominant polycystic kidney disease including the $CD1^{pcy/pcy}$ mouse model (Gattone et al., Nature Medicine, 2003, 9, 1323-1326; Torres, V. E., Clin. J. Am. Soc. Nephrol., 2008, 3, 1212-1218; Wang et al., J. Am. Soc. Nephr., 2008, 19, 102-108). The $CD1^{pcy/pcy}$ mouse is a model for autosomal recessive cystic kidney disease that is caused by a missense mutation in the NPHP3 gene which encodes nephrocystin-3, a protein involved in renal tubular development and function. This mutation leads to renal cyst formation and end-stage renal failure. Moreover, phase III clinical trials on patients with autosomal dominant polycystic kidney disease showed that Tolvaptan administered to patients during 3 years decreased proliferation of cyst-lining epithelial cells (Higashihara et al., Clin. J. Am. Soc. Nephrol., 2011, 6, 2499-2507).

Cancer

By interacting with arrestin V2R stimulation leads to the activation of signaling pathways involving cAMP and MAP kinase thus favoring a proliferative response. For example, AVP injection in the rat induces the proliferation of renal tubular epithelial cells that can be inhibited by V2R antagonists (Alonso et al., Endocrinology, 2009, 150, 239-250). Moreover, diuretics such as V2R antagonists were able to inhibit the proliferation of renal cancer cells (Bolignano et al., Urol. Oncol., 2010, 28, 642-647) and of pulmonary cancer cells (Pequeux et al., Endocr. Relat. Cancer, 2004, 11, 871-885. These results indicate that V2R antagonists are good therapeutic candidates against different types of cancer.

Thrombosis

The Von Willebrand factor (VWF) is implicated in primary hemostasis. It has been demonstrated that AVP and also the V2R specific agonist, dDAVP (Minirin®), increases VWF and factor VIII levels via their interaction with V2R (Kaufmann et al., J. Clin. Invest., 2000, 106, 107-116). An excess in coagulation can lead to thrombosis (clots) which could be cured by the use of V2R antagonists thus limiting the secretion of coagulation factors.

Ménière Disease

In France, the incidence of Ménière disease is estimated to be 1/13,300. Its pathogenesis is largely unknown. Endolymphatic swelling is considered a pathognomonic sign. It may result either from endolymph hypersecretion or from insufficient reabsorption. Menière pathology of the inner ear seems to be the origin for symptoms such as vertigo, nausea, tinnitus and hearing loss. It is believed that the increased pressure in the cochlea compromises the ability of cilial cells to detect correctly the soundwave or movements (Kitahara et al., J. Neuroendocrinol., 2008, 20, 1295-1300). Presently, treatment with acetazolamide (diamox) is used which inhibits carbonic anhydrase and acts as hypokaliemic diuretic. By reducing the osmotic pressure into the inner ear, V2R could be used for treating Ménière disease.

Although vaptans have clearly proven the therapeutic effect of V2R antagonists on various pathologies, their therapeutic use is limited by some major drawbacks:

- Vaptans are hepatotoxic due to their inhibitory effect on cytochrome CYP3A4. For this reason, their use necessitates a tight monitoring of the patients and their long-term administration is limited. Some of them are only injected intravenously which restrict their use to hospitalized patients.
- Vaptans have some selectivity only for V2R with V2/V1a selectivity index which varies from 112 (Satavaptan) to 0.15 (Conivaptan).
- Vaptans are agonists for MAP kinase activation. Therefore, they are unable to block completely specific V2R-associated signaling pathways.
- Vaptans are poorly soluble in physiological buffers and have limited bioavailability (Bernier et al., JASN, 2006, 17, 591-).

Therefore, there is a need for new V2R antagonists with improved properties for therapeutic use, particularly with increased V2R selectivity and reduced toxicity, compared to currently available non-peptidic V2R antagonists.

Kunitz domains are the active domains of Kunitz-type protease inhibitors. They are relatively small with a length of about 50 to 60 amino acids and a structure which is a disulfide rich alpha and beta fold. The majority of the sequences having this domain belong to the kunitzbovine pancreatic trypsin inhibitor family which includes bovine pancreatic trypsin inhibitor (BPTI or basic protease inhibitor) and numerous other members such as snake venom basic protease inhibitors like dendrotoxins, mammalian inter-alpha-trypsin inhibitors, trypstatin, a domain found in an alternatively spliced form of Alzheimer's amyloid protein, domains at the C-termini of the alpha-1 and alpha-3 chains of type VI and type VII collagens, tissue factor pathway inhibitor precursor and Kunitz STI protease inhibitor contained in legume seeds.

Dendrotoxins are a group of neurotoxins isolated from the venom of the black mamba (*Dendroaspis polyepis polyepis*) and the eastern green mamba (*Dendroaspis angusticeps*) that are selective blockers of particular subtypes of voltage-gated potassium channels in neurons, thereby enhancing the release of acetylcholine at neuromuscular junctions. Because of their high potency and selectivity for potassium channels, dendrotoxins represent useful pharmacological agents for studying the structure and function of these ion channel proteins and for treating human diseases (WO 2007019267). Dentrotoxins are small proteins consisting of a single peptide chain of less than 100 amino acids, generally of about 57-60 amino acids, that folds into the Kunitz structure, i.e., a disulfide rich alpha and beta fold composed of 3 disulfide bridges with the connectivity 1-6, 2-4, 3-5 and arranged to form a twisted two-stranded antiparallel beta sheet followed by an alpha helix (Berndt et al., J. Mol. Biol., 1993, 234, 735-750).

SUMMARY

The inventors have isolated a novel toxin from the green mamba venom and they have demonstrated that this toxin, named U-Da2a, which is a member of the snake venom basic protease inhibitors of the kunitzbovine pancreatic trypsin inhibitor family, is a competitive and selective V2R antagonist. They have also found that the amino acid motif in positions 15 to 18 of U-Da2a sequence is essential for the competitive antagonist activity of U-Da2a for V2R and that other snake venom basic protease inhibitors having a similar motif at these positions are also V2R antagonists, while snake venom basic protease inhibitors not having this motif are not V2R antagonists. These results allow to define a new group of snake venom basic protease inhibitors having V2R antagonist activity, which includes novel and known dendrotoxins having this specific amino acid motif.

As peptide antagonist of V2R, the proteins of this group of snake venom basic protease inhibitors can be used for various applications including therapy, diagnosis, treatment response prediction, medical imaging, drug screening and research. In particular, these proteins provide good therapeutic candidates for the treatment of pathologies involving the V2R pathway such as hyponatremia and polycystic kidney disease.

One aspect of the invention relates to an isolated protein, comprising an amino acid sequence (I) which is at least 50% identical to residues 1 to 57 of SEQ ID NO: 1, and which comprises:

(i) a motif $X_1X_2X_3X_4$ in positions 15 to 18 of SEQ ID NO: 1, wherein $X_1$ is an asparagine (N), $X_2$ is a glycine (G), $X_3$ and $X_4$ are hydrophobic amino acids or $X_1$ is a methionine (M), $X_2$ and $X_3$ are phenylalanines (F), and $X_4$ is an Isoleucine (I), and (ii) one to three disulfide bonds between two cysteine residues, for use as vasopressin-2 receptor (V2R) antagonist in the treatment of diseases involving the V2R pathway.

In the following description, the standard one letter amino acid code is used. Hydrophobic amino acids refer to M, W, F, A, V, L, I, Y and P.

The protein for the different uses according to the invention, which may be natural, recombinant or synthetic, comprises or consists of an amino acid sequence (I), The sequence (I) is a pharmacologically active toxin having competitive V2R antagonist activity, named protein, peptide, or toxin. The protein for the different uses according to the invention has the typical Kunitz-type structure of dendrotoxins, which is a twisted two-stranded antiparallel beta sheet followed by an alpha helix, and comprises one to three disulfide bonds to stabilize the protein and contribute to its structural conformation.

These properties can be readily verified by technique known to those skilled in the art such as those described in the examples of the present application.

The invention encompasses the use of a protein comprising or consisting of natural amino acids (20 gene-encoded amino acids in a L- and/or D-configuration) linked via a peptide bond as well as peptidomimetics of such protein where the amino acid(s) and/or peptide bond(s) have been replaced by functional analogues. Such functional analogues include all known amino acids other than said 20 gene-encoded amino acids. A non-limitative list of non-coded amino acids is provided in Table 1A of U.S. 2008/0234183 which is incorporated herein by reference. The invention also encompasses modified proteins derived from the above proteins by introduction of any modification into one or more amino acid residues, peptide bonds, N- and/or C-terminal ends of the protein, as long as the V2R antagonist activity is maintained in the modified protein. These modifications which are introduced into the protein by the conventional methods known to those skilled in the art, include, in a non-limiting manner: the substitution of a natural amino acid with a non-proteinogenic amino acid (D amino acid or amino acid analog); the modification of the peptide bond, in particular with a bond of the retro or retro-inverso type or a bond different from the peptide bond; the cyclization, and the addition of a chemical group to the side chain or the end(s) of the protein, in particular for coupling an agent of interest to the protein of the invention. These modifications may be used to label the protein, and to increase its affinity for V2R, its bioavailability and/or its stability.

The percent amino acid sequence identity is defined as the percent of amino acid residues in a Compared Sequence that are identical to the Reference Sequence SEQ ID NO: 1 after aligning the sequences and introducing gaps if necessary, to achieve the maximum sequence identity. The Percent identity is then determined according to the following formula: Percent identity=100×[1-(C/R)], wherein C is the number of differences between the Reference Sequence SEQ ID NO: 1 and the Compared sequence over the entire length of SEQ ID NO: 1 (i.e., positions 1 to 57 of SEQ ID NO: 1), wherein (i) each amino acid in the Reference Sequence that does not have a corresponding aligned amino acid in the Compared Sequence, (ii) each gap in the Reference Sequence, and (iii) each aligned amino acid in the Reference Sequence that is different from an amino acid in the Compared Sequence constitutes a difference; and R is the number amino acids in the Reference Sequence over the length of the alignment with the Compared Sequence with any gap created in the Reference Sequence also being counted as an amino acid.

Alignment for purposes of determining percent amino acid sequence identity can be achieved in various ways known to a person of skill in the art, for instance using publicly available computer software such as BLAST (Altschul et al., J. Mol. Biol., 1990, 215, 403-). When using such software, the default parameters, e.g., for gap penalty and extension penalty, are preferably used. For amino acid sequences, the BLASTP program uses as default a word length (W) of 3 and an expectation (E) of 10.

For example, the alignment of Blackelin-3 (SEQ ID NO: 5; 83 amino acids) with U-Da2a (SEQ ID NO: 1) presented on FIG. 1B, shows that over the length of alignment between the Reference Sequence and the Compared Sequence, i.e., the entire length of SEQ ID NO: 1 (positions 1 to 57 of SEQ ID NO: 1), there are no gap in the Reference Sequence, no gap in the Compared Sequence and 23 amino acid in the Reference Sequence which are different from the aligned amino acid sequence in the Compared Sequence. Therefore, C=23 and R=57. The percent identity=100× [1-(23/57)]. Blackelin-3 comprises an amino acid sequence which is 60% identical to positions 1 to 57 of SEQ ID NO: 1.

In a preferred embodiment, the protein comprises or consists of an amino acid sequence (I) which is at least 55%, 60%, 65%, 70%, 75%, 80%, 85%, 90% or 95% identical to residues 1 to 57 of SEQ ID NO: 1. Preferably, the sequence (I) is at least 60% identical to residues 1 to 57 of SEQ ID NO: 1. More preferably, it is at least 65% identical to residues 1 to 57 of SEQ ID NO: 1.

In another preferred embodiment, the sequence (I) comprises a motif $X_1X_2X_3X_4$ selected from the group consisting of NGFF and NGLF.

In another preferred embodiment, the sequence (I) has up to 100 amino acids, more preferably about 60 amino acids, and is selected from the group consisting of SED ID NO: 1 and a sequence which differs from SEQ ID NO: 1 by dispersed deletions and/or insertions of one to five amino acids in SEQ ID NO: 1, and/or substitutions and/or terminal deletion (s) of 1 to 30, preferably 1 to 15, 1 to 10 or 1 to 5 amino acids.

The deletion(s) and/or insertion(s) are advantageously chosen from: (i) one to five single amino acid deletion(s) insertions(s) dispersed in SEQ ID NO: 1, and (ii) terminal deletion(s) of 1 to 5 amino acids at one or both ends of SEQ ID NO: 1. Preferably the terminal deletion(s) are chosen from an N-terminal deletion of 1, 2, 3 or 4 amino acid residues and/or a C-terminal deletion of 1 or 2 amino acid residues of SEQ ID NO: 1.

The substitution(s) in SEQ ID NO:1 are advantageously chosen from 1 to 10, preferably 1 to 5 conservative substitutions, i.e., substitutions of one amino acid with another which has similar chemical or physical properties (size, charge or polarity), which generally does not modify the functional properties of the protein. More preferably, said conservative substitution(s) are chosen within one of the following five groups: Group 1-small aliphatic, non-polar or slightly polar residues (A, S, T, P, G); Group 2-polar, negatively charged residues and their amides (D, N, E, Q); Group 3-polar, positively charged residues (H, R, K); Group 4-large aliphatic, nonpolar residues (M, L, I, V, C); and Group 5-large, aromatic residues (F, Y, W).

The cysteine residues in positions 5 and 55, 14 and 38, and/or 30 and 51 of SEQ ID NO: 1 are advantageously not mutated.

Preferably, the protein comprises or consists of a sequence selected from the group consisting of: the amino acid sequences SEQ ID NO: 1 to 5, a variant of any one of SEQ ID NO: 1 to 3 comprising an N-terminal deletion of 1, 2, 3 or 4 amino acid residues and/or a C-terminal deletion of 1 or 2 amino acid residues, and a variant of SEQ ID NO: 5 or 6 comprising an N-terminal deletion of one to thirty amino acid residues and/or a C-terminal deletion of one or two amino acid residues. Examples of such preferred proteins are SEQ ID NO: 11 to 13.

In another preferred embodiment, the sequence (I) comprises one to three (one, two or three), preferably three, disulfide bonds chosen from disulfide bonds between C1 and C6, C2 and C4, and C3 and C5, wherein C1 to C6 are each a cysteine residue, numbered respectively from the N-terminus to the C-terminus of said sequence (I). Examples of such proteins are SEQ ID NO: 1 and 16, which comprise three and two disulfide bonds, respectively. Preferably, C1 is in positions 1 to 31, more preferably 1 to 15, 1 to 10 or 1 to 5 (1, 2, 3, 4 or 5) of said sequence (I) and is separated from C6 by 50±2 amino acids; C2 and C4, C3 and C5 are separated by 25±2 and 20±2 amino acids, respectively. More preferably, C1 to C6 are in positions 5, 14, 30, 38, 51 and 55, respectively of SEQ ID NO: 1. In addition, C1 and/or C6 are advantageously the first and the last residues, respectively of said protein.

In another preferred embodiment, the protein is a modified protein lacking the four N-terminal and the two C-terminal residues of SEQ ID NO: 1, wherein the NH2 function of C1 is chemically blocked, for example by acetylation and the COOH function of C6 is also chemically blocked, for example by amidation. The peptide is a cyclic peptide, known to be much more resistant to exo-proteases.

In another preferred embodiment, the protein is a modified protein wherein one or more amino acid residues targeted by endoproteases are replaced by their corresponding non-natural D-form. For example, one or more arginine and/or lysine residues which are targets for trypsin can be replaced by their corresponding non-natural form.

In another preferred embodiment, the protein is a modified protein, wherein one or more disulfide bridges are replaced by non-natural links. Preferably, said non-natural link is resistant to reduction, such as, for example, a thiazolidine linker. These linkers increase the resistance of the protein of the invention to reducing agents present in biologic fluids.

In another preferred embodiment, the protein is a fusion or chimeric protein, comprising a sequence (II) fused to one end of the sequence (I) and, optionally, another sequence (III) fused to the other end of said sequence (I). The length of the protein is not critical to the invention as long as the V2R antagonist activity is maintained. The sequences (II) and (III) comprise one or more other protein/peptide moieties including those which allow the purification, detection, immobilization, and/or cellular targeting of the protein of the invention, and/or which increase the affinity for V2R, the bioavailability, the production in expression systems and/or stability of said protein. These moieties may be selected from: (i) a labeling moiety such as a fluorescent protein (GFP and its derivatives, BFP and YFP), (ii) a reporter moiety such as an enzyme tag (luciferase, alkaline phosphatase, glutathione-S-transferase (GST), (β-galactosidase), (ii) a binding moiety such as an epitope tag (polyHis6, FLAG, HA, myc.), a DNA-binding domain, a hormone-binding domain, a poly-lysine tag for immobilization onto a support, (iii) a stabilization moiety such as ZZ, DsBa and DsBb, and (iv) a targeting moiety for addressing the chimeric protein to a specific cell type or cell compartment. In addition, the sequence(s) (II) and/or (III) advantageously comprise a linker which is long enough to avoid inhibiting interactions between sequence (I) and sequences (II) and/or (III). The linker may also comprise a recognition site for a protease, for example, for removing affinity tags and stabilization moieties from the purified chimeric protein according to the present invention.

In another preferred embodiment, the protein is coupled to an agent which increases its bioavailability, and in particular reduces its urinary elimination, such as, for example, polyethylene glycol.

The invention encompasses the use of a polynucleotide encoding the protein in expressible form or a recombinant vector comprising said polynucleotide. The polynucleotide encoding the protein in expressible form refers to a nucleic acid molecule which, upon expression in a cell or a cell-free system results in a functional protein.

According to the invention, the protein, polynucleotide and/or vector may be included in a pharmaceutical composition, further comprising a pharmaceutically acceptable carrier.

The pharmaceutical composition is formulated for administration by a number of routes, including but not limited to oral, parenteral and local. The pharmaceutically acceptable carriers are those conventionally used.

In addition, the protein may advantageously be modified by means well-known to those skilled in the art, in order to change its physiological properties, and in particular in order to improve its half-life time in the organism (glycosylation: HAUBNER R. et al., J. Nucl. Med., 2001, 42, 326-36; conjugation with PEG: KIM T H. et al., Biomaterials, 2002, 23, 2311-7), its solubility (hybridization with albumin: KOEHLER M F. et al., Bioorg. Med. Chem. Lett., 2002, 12, 2883-6), its resistance to proteases (unnatural amino acids (D conformation, for example)), and/or its intestinal absorption (Lien et al., TIB, 2003, 21, 556-).

The pharmaceutical composition comprises a therapeutically effective amount of the proteinpolynucleotidevector, e.g., sufficient to show benefit to the individual to whom it is administered. The pharmaceutically effective dose depends upon the composition used, the route of administration, the type of mammal (human or animal) being treated, the physical characteristics of the specific mammal under consideration, concurrent medication, and other factors, that those skilled in the medical arts will recognize.

The invention provides also a method for treating a patient in need for treatment of a pathology involving the V2R pathway, comprising: administering a therapeutically effective amount of the protein, polynucleotide and/or vector to the patient.

Pathologies involving the V2R pathway include, with no limitations: (i) pathological conditions characterized by euvolemic or hypovolemic hyponatremia, such as congestive heart failure (CHF), cirrhosis, Syndrome of Inappropriate AntiDiuretic Hormone secretion (SIADH) and cerebral oedema, (ii) Nephrogenic Syndrome of Inappropriate Antidiuresis (NSIAD), (iii) Congenital Nephrogenic Diabetes Insipidus (cNDI), (iv) Polycystic kidney disease, (v) cancers, including renal and lung cancers, (vi) thrombosis, and (vii) Menière disease.

Another aspect of the invention relates to the use of the protein as a diagnostic or imaging reagent that can be applied in optical imaging, magnetic resonance imaging (MRI) and positron emission tomography (PET) for detecting V2R in situ (in vitro or in vivo) under physiological or pathological conditions or in response to an endogenous or exogenous stimulus, for diagnostic or research purposes. The protein is also used as a drug screening tool, for screening V2R ligands, including V2R agonists and antagonists.

In a preferred embodiment, the protein is coupled to a labeling agent which produces a detectable and/or quantifiable signal, in particular a radioactive, magnetic or luminescent (radioluminescent, chemiluminescent, bioluminescent, fluorescent or phosphorescent) agent. The labeled protein may be labeled directly or indirectly, via covalent or non-covalent bonds, using standard conjugation techniques that are well-known to those skilled in the art. Examples of labeling agents include radioactive isotopes such as Technetium-99 ($^{99}Tc$), Fluorine 18 ($^{18}F$), Tritium ($^{3}H$) and Iodine ($^{125}I$); luminescent agents such as AlexaFluor, FITC and cyanine 3; paramagnetic contrast agents such as gadolinium compounds, and superparamagnetic contrast agents such as iron oxide nanoparticles.

In a more preferred embodiment, the labeled protein is linked covalently to a radioactive or a fluorescent agent.

Covalent coupling of the labeling agent, for example a fluorescent or radioactive agent, to the protein may be achieved by: (i) incorporating the labeling agent at the N- or C-terminal end of the protein during chemical synthesis of the protein, or (ii) incorporating a reactive group (free cysteine, biotinin, azido moiety) in a recombinant or synthetic protein, and then using the group to link the labeling agent covalently.

Preferably, the labeling agent is linked covalently to the N- or C-terminus of the protein as the extremities of the protein are not implicated in its binding to V2R.

A subject of the present invention is also the use of the protein, in vitro, for diagnosing a pathology involving an increase or decrease in V2R expression level.

Another subject of the present invention is the protein for use, in vivo, for diagnosing a pathology involving an increase or decrease in V2R expression level For diagnostic applications, the labeled protein is used to visualize V2R expression, in situ, in a tissue from a patient, and evaluate its expression level in comparison to the same type of tissue from an healthy individual. V2R overexpression is indicative of a pathological condition such as cancer, whereas V2R underexpression is indicative of a pathological condition such as Congenital Nephrogenic Diabetes Insipidus (cNDI). Once, the diagnostic has been established, it is possible to decide on an effective treatment for the diagnosed patient, including the use of V2R antagonists, for example for treating cancer or cNDI.

A subject of the present invention is also the use of the protein, as a research tool for studying V2R.

Another subject of the present invention is a method for detecting V2R, in vitro and in vivo, comprising at least the steps of:

- bringing cells to be analyzed into contact with the labeled protein, and
- detecting the labeled cells.

The labeling of the cells is in particular fluorescent labeling or magnetic labeling, detectable by any technique known to those skilled in the art (fluorescence microscopy, flow cytometry, magnetic resonance imaging).

The detection of the receptors, in vivo, in the body of a mammal (cell imaging), in particular in real time, comprises a prior step of administering said peptide to said mammal (parenteral injection, oral administration).

Another subject of the present invention is the use of the protein for screening V2R ligands.

A subject of the present invention is also a method for screening V2R ligands, comprising:

- incubating V2R with a test molecule and the labeled protein, and
- measuring the signal obtained in the presence and absence of the test molecule, wherein a lower signal in the presence of the molecule compared to the control without the test molecule indicates that the test molecule is a V2R ligand.

The agonist, antagonist effect of the identified ligands on V2R are then tested in cells expressing V2R using pharmacological assays which are well-known in the art such as those disclosed in the examples of the present application.

Another subject of the present invention is the use of the protein as a crystallization agent for producing V2R crystals. V2R crystals are then analyzed by X-ray diffraction to determine V2R three-dimensional structure.

Another aspect of the invention is an isolated protein comprising an amino acid sequence (I) which is at least 70% identical to residues 1 to 57 of SEQ ID NO: 1 and comprises: (i) a motif $X_1X_2X_3X_4$ in positions 15 to 18 of SEQ ID NO: 1, wherein $X_1$ is an asparagine (N), $X_2$ is a glycine (G), $X_3$ and $X_4$ are hydrophobic amino acids, and (ii) at least one disulfide bond between two cysteine residues, and wherein said protein has V2R antagonist activity.

The protein of the invention comprises the protein of SEQ ID NO: 1, named as U-Da2a, U-Da2a protein, U-Da2a peptide or U-Da2a toxin.

The protein of the invention belongs to a subgroup of the group of proteins which is used in the present invention. Therefore, the protein of the invention has the characteristic Kunitz fold of snake venom basic protease inhibitors and V2R antagonist activity. The protein of the invention is a natural, recombinant or synthetic protein that may be modified, chimeric, and/or labeled as explained before for the proteins used in the present invention.

The protein of the present invention possesses the following advantageous features other the known non-peptide V2R antagonists:

- it is a highly selective ligand of the V2R with absolute selectivity for the V2R versus 150 other GPCRs and 8 cardiac ionic channels. For example, U-Da2a has a V2R/V1a selectivity index which is superior to 10,000. A combined high affinity and strong selectivity may allow to reduce therapeutic doses and consequently secondary side effects.
- it has nanomolar affinities for the V2R.
- it is the first selective and competitive antagonist which is able to block the three major signaling pathways of V2R, i.e., cAMP accumulation, arrestin recruitment and MAP kinase phosphorylation, and as such may lead to a new class of therapeutics,
- it is able to reach the V2R target in vivo and to produce a strong diuretic effect without any toxicity using a daily saturating dose during at least 90 days.
- As a peptide, it shows additional interesting properties: no toxicity from peptide degradation products, a perfect water solubility, it should not cross the blood-brain barrier and so should not affect the function of receptors in the central nervous system, and it is a lead chemical structure for the generation of diagnostic tools.

In a preferred embodiment, the protein of the invention comprises or consists of an amino acid sequence (I) which is at least 75%, 80%, 85%, 90% or 95% identical to residues 1 to 57 of SEQ ID NO: 1.

In another preferred embodiment, the sequence (I) has up to 75 amino acids, more preferably about 60 amino acids, and is selected from the group consisting of SED ID NO: 1 and a sequence which differs from SEQ ID NO: 1 by the deletion, insertion, and/or substitution of 1 to 15, preferably 1 to 10, more preferably 1 to 5 amino acids.

The deletion(s) and/or insertion(s) are advantageously chosen from: (i) one to five single amino acid deletion(s) insertions(s) dispersed in SEQ ID NO: 1, and (ii) terminal deletion(s) of 1 to 5 amino acids at one or both ends of SEQ ID NO: 1. Preferably the terminal deletion(s) are chosen from an N-terminal deletion of 1, 2, 3 or 4 amino acid residues and/or a C-terminal deletion of 1 or 2 amino acid residues of SEQ ID NO: 1.

The substitution(s) in SEQ ID NO:1 are advantageously chosen from 1 to 10, preferably 1 to 5 conservative substitutions. The cysteine residues in positions 5 and 55, 14 and 38, and/or 30 and 51 of SEQ ID NO: 1 are advantageously not mutated.

Preferably, the protein of the invention comprises or consists of the amino acid sequence SEQ ID NO: 1 or a variant of SEQ ID NO: 1 comprising an N-terminal deletion of 1, 2, 3 or 4 amino acid residues and/or a C-terminal deletion of 1 or 2 amino acid residues. Examples of such preferred proteins are SEQ ID NO: 11 to 13.

In another preferred embodiment, the sequence (I) comprises one to three (one, two or three), preferably three, disulfide bonds chosen from disulfide bonds between C1 and C6, C2 and C4, and C3 and C5, wherein C1 to C6 are each a cysteine residue, numbered respectively from the N-terminus to the C-terminus of said sequence (I). Examples of such proteins are SEQ ID NO: 1 and 16, which comprise three and two disulfide bonds, respectively. Preferably, C1 is in positions 1 to 5 (1, 2, 3, 4 or 5) of said sequence (I) and is separated from C6 by 50±2 amino acids; C2 and C4, C3 and C5 are separated by 25±2 and 20±2 amino acids, respectively. More preferably, C1 to C6 are in positions 5, 14, 30, 38, 51 and 55, respectively of SEQ ID NO: 1. In addition, C1 and/or C6 are advantageously the first and the last residues, respectively of said protein.

Another aspect of the invention relates to an isolated polynucleotide encoding a protein of the invention. The synthetic or recombinant polynucleotide may be DNA, RNA or combination thereof, either single- and/or double-stranded. Preferably the polynucleotide comprises a coding sequence which is optimized for the host in which the protein is expressed.

Another aspect of the invention relates to a recombinant vector comprising said polynucleotide. Preferably, said recombinant vector is an expression vector capable of expressing said polynucleotide when transfected or transformed into a host cell such as a mammalian, bacterial or fungal cell. The polynucleotide is inserted into the expression vector in proper orientation and correct reading frame for expression. Preferably, the polynucleotide is operably linked to at least one transcriptional regulatory sequence and, optionally to at least one translational regulatory sequence. Recombinant vectors include usual vectors used in genetic engineering and gene therapy including for example plasmids and viral vectors.

A further aspect of the invention provides a host cell transformed with said polynucleotide or recombinant vector.

The polynucleotide, vector, cell of the invention are useful for the production of the protein of the invention using well-known recombinant DNA techniques.

Another aspect of the invention relates to a pharmaceutical composition, comprising at least one protein, polynucleotide and/or vector of the invention, and a pharmaceutically acceptable carrier. A further aspect of the invention relates to a protein, polynucleotide, and/or vector of the invention as a medicament.

Another aspect of the invention related to a diagnostic reagent comprising a protein of the invention, preferably a labeled protein.

The invention provides also a kit comprising: (a) a container that contains one or more of: a protein, polynucleotide, recombinant vector, modified host cell, pharmaceutical composition, diagnostic or imaging reagent of the invention, in solution or in lyophilized form; (b) optionally, a second container containing a diluent or reconstituting solution for the lyophilized formulation; (c) optionally a third container containing an isolated V2R receptor or host cell capable of expressing V2R in solution or in lyophilized form, and optionally instructions for the use of the solution(s) and/or the reconstitution and/or use of the lyophilized formulation(s).

The V2R according to the invention is from any mammal. Preferably, it is human V2R.

The polynucleotide according to the invention is prepared by the conventional methods known in the art. For example, it is produced by amplification of a nucleic sequence by PCR or RT-PCR, by screening genomic DNA libraries by hybridization with a homologous probe, or else by total or partial chemical synthesis. The recombinant vectors are constructed and introduced into host cells by the conventional recombinant DNA and genetic engineering techniques, which are known in the art.

The protein is prepared by the conventional techniques known to those skilled in the art, in particular by solid-phase or liquid-phase synthesis or by expression of a recombinant DNA in a suitable cell system (eukaryotic or prokaryotic). More specifically, the protein and its derivatives can be solid-phase synthesized, according to the Fmoc technique, originally described by Merrifield et al. (J. Am. Chem. Soc., 1964, 85: 2149-), and purified by reverse-phase high performance liquid chromatography; the protein and its derivatives, can also be produced from the corresponding cDNAs, obtained by any means known to those skilled in the art; the cDNA is cloned into a eukaryotic or prokaryotic expression vector and the protein produced in the cells modified with the recombinant vector is purified by any suitable means, in particular by affinity chromatography.

The practice of the present invention will employ, unless otherwise indicated, conventional techniques which are within the skill of the art. Such techniques are explained fully in the literature.

BRIEF DESCRIPTION OF THE DRAWINGS

In addition to the above arrangements, the invention also comprises other arrangements, which will emerge from the description which follows, which refers to exemplary embodiments of the subject of the present invention, with reference to the attached drawings in which:

FIG. 1 represents the sequence alignment of U-Da2a with other known toxins. A. Dendrotoxin-B (Dtx-B Ala 27 or Dtx-B-A27; SWISSPROT P00983.1; SEQ ID NO: 2); Dendrotoxin-E His55 (DTx-E-H55; SWISSPROT P00984.1; SEQ ID NO: 6); Mulgin-1 (GenBank AAT45400.1; SEQ ID NO: 4); Blackelin-3 (GenBank ABV64393; SEQ ID NO: 5); Dendrotoxin-K (Dtx-K; SWISSPROT P00981.2; SEQ ID NO: 8); Alpha-Dendrotoxin (Alpha-Dtx; SWISSPROT P00980.1; SEQ ID NO: 9); Bovine Pancreatic trypsin inhibitor (BPTI; SWISSPROT P00974.2; SEQ ID NO: 10). Percent identity is indicated on the right. B. Alignment of U-Da2a with Blackelin-3 illustrating percent identity determination.

FIG. 13 illustrates the effect of U-Da2a on cyst numbers in $CD1^{pcy/pcy}$ mice after 99 days of daily toxin injections at 0.1 μmol/kg i.p. Mice were perfusion-fixed with 4% paraformaldehyde/1× phosphate-buffered saline, kidneys were removed and embedded in paraffin. A. Transverse kidney sections were stained with hematoxylin and eosin. B. Cyst number was determined using the program ImageJ and related to the size of the section thus arriving at the relative cyst number. U-Da2a (grey box). Control (0.9% NaCl; black box).

DETAILED DESCRIPTION

Example 1

U-Da2a Preparation and Biochemical Characterization

Figure 2:
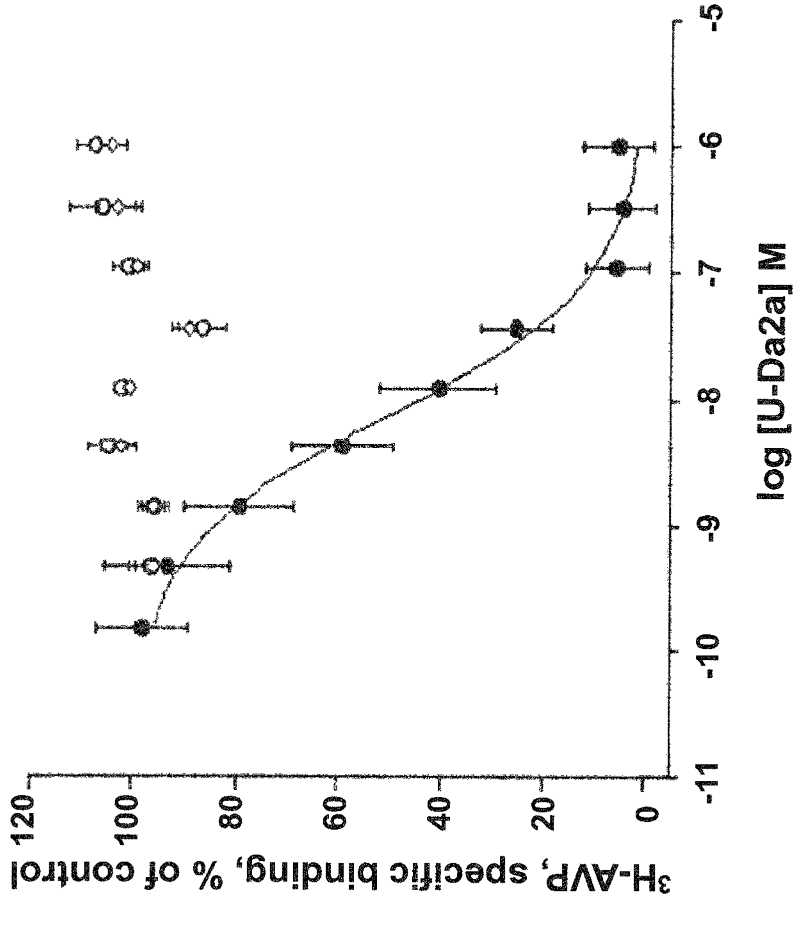
FIG. 2 illustrates $^{3}$H-AVP binding inhibition by U-Da2a on the different vasopressin receptor subtypes expressed in eukaryotic cells. (○) V1aR. (◇) V1bR. (■) V2R.

1) Materials and Methods a) Protein Extraction and Purification

One gram of *Dendroaspis angusticep* venom (LATOXAN, France) was separated into 13 fractions by ion exchange (2×15 cm) on Source 15S using a multi-step NaCl gradient at 2 mL/min on an Akta purifier (PFIZER, Canada). Fraction F was further purified by reverse-phase chromatography (Waters 600) on a preparative column (C18, 15 μm, 20 cm, VYDAC, France, 20 mL/min), using a linear gradient from 0 to 100% acetonitrile and 0.1% trifluoroacetic acid in 100 min Fraction D was finally purified on a C18 Vydac column (4.6 mm, 5 μm, 15 cm 1 mL/min) using a gradient of 0.5% acetonitrilemin.

b) Biochemical Characterization

Sequencing of U-Da2a by Edman Degradation

N-terminal sequencing of U-Da2a (200 pmol loaded on a Biobrene-coated filter) was carried out using Edman chemistry on a Procise Model 492 automatic sequencer from Applied Biosystems (Foster City, Calif. USA).

Sequencing by In-Source Decay MALDI-TOF

15 μg of purified U-Da2a was reduced with 2 μL of tris(carboxyethyl)phosphine 100 mM (SIGMA-ALDRICH, St Louis, USA) to remove the disulfide bonds. After 1 hour at 50° C., the mixture was purified on a Zip-Tip $C_{18}$ microcolumn (MILLIPORE, Billarica, Mass., USA) according to the manufacturer protocol. Elution of the reduced toxin was performed with 5 μL of acetronitrile/formic acid (ACN/FA) 0.2% (50/50, vv). 1,5-Diaminonaphthalene (ACROS, Geel, Belgium) saturated in acetronitrile formic acid 0.1% 50/50 (vv), was used as the matrix for in-source decay experiments. 1 μL of the toxin solution and 1 μL of the matrix were mixed together and spotted onto a MALDI plate. In-Source-Decay (ISD) fragmentation was recorded with an ULTRAFLEX II MALDI-TOF/TOF (BRUKER DALTONICS, Bremen, Germany) mass spectrometer equipped with a Nd-YAG Smartbeam laser (MLN 202, LTB). Spectra were acquired between m/z 900 and 6500 with a laser power set at 55%.

Digestion, Peptide Mass Fingerprint and C-ter Characterization of U-Da2a 300 ng of purified toxin were dissolved in 5 μL of 50 mM $NH_4HCO_3$ (pH 8). 2 μL of 250 mM dithiothreitol (DTT) were then added to reduce all the disulfide bonds (30 min at 56° C.). Sulfhydryl groups were then alkylated with 2.2 μL of 500 mM iodoacetamide (IAA) during one hour, in dark, at room temperature. Both DTT and IAA were preliminary prepared in 50 mM $NH_4HCO_3$. 10 ng of bovine trypsin (ratio 1/30) were finally added to digest U-Da2a, during 4 hours at 37° C. The resulting peptides were desalted with a Zip-Tip $C_{18}$ microcolumn and eluted with 10 μL of ACN/FA 0.2% (50/50, v/v). 1 μL of this sample was spotted on the MALDI plate and mixed together with 1 μL of 2,5-dihydroxybenzoic acid (2,5-DHB) used as the matrix. The analysis of the peptides was made with the ULTRAFLEX II spectrometer (see above). Peptide mass fingerprint was recorded from m/z 500 to 3600. Tandem mass spectrometry experiments were performed using LIFT-TOF/TOF technology (Detlev et al., Suckau, Anal. Bioanal. Chem., 2003, 376, 952-965).

Software

All the data were acquired thanks to Flex Control 3.0. Resulting spectra were analyzed with Biotools 3.2 and Sequence Editor 3.2. The three softwares are from BRUKER DALTONICS.

c) Protein Synthesis and Processing

U-Da2a was synthesised on an APPLIED BIOSYSTEMS 433A peptide synthesiser (Foster City, Calif., USA), purified and folded according to the method described for the muscarinic toxin MT1 (Mourier et al., Mol Pharmacol, 2003, 63, 26-35). Briefly, this involved solid-phase synthesis using a Fmoc strategy, peptide cleavage and purification on a reverse-phase column. The linear peptide was then folded for 24 h in the presence of glycerol (25%) and oxidised and reduced glutathione (1 mM) in Tris buffer at pH 8.

2) Results

The presence of a toxin able to bind V2R was detected by screening of venom extracted from the snake *Dendroaspis angusticeps*. Once purified, this toxin was sequenced by two complementary procedures, Edman degradation and mass fragmentation, and biochemically characterized.

The toxin, named U-Da2a, is a 57 amino-acid peptide: RPSFCNLPVKPGPCNGFFSAFYYSQKTNKCHSFTYGGCKGNANRFSTIEKCRR TCVG (SEQ ID NO: 1) with 3 disulfide bonds (Cys1-Cys6, Cys2-Cys4 and Cys3-Cys5) belonging to the Kunitz structural family. The nearest sequences correspond to other snake toxins such as dendrotoxins E, B and K, Mulgin-1 and Blakelin-3 (FIG. 1). These dendrotoxins have the property to block voltage-dependent potassium channels.

Solid phase peptide synthesis allows the synthesis of large quantities of U-Da2a in GMP quality. The synthetic peptide was then processed in order to form disulfide bridges. This synthetic compound which has the same pharmacological properties as the natural product was used in all the following experiments.

Example 2

U-Da2a Selectivity Profile

1) Materials and Methods 1.1 Binding Assays with Vasopressin Receptors

Membranes from cells expressing vasopressin receptors were purchased from PERKINELMER (Courtaboeuf, France). Binding experiments were performed with $^3$H-AVP (PERKINELMER, Courtaboeuf, France) in 96-well plates. Reaction mixtures contained 50 mM Tris-HCl, pH 7.4, 10 mM $MgCl_2$ and 1 g/L BSA in a final volume of 100 μL. Plates were incubated for 3 h at room temperature. Binding reactions were stopped by filtration through a GF/C filter pre-soaked in 0.5% polyethyleneimine on a cell harvester (PERKINELMER, Courtaboeuf, France) and plates were dried. Ultimagold O (25 μl; PERKINELMER) was added to each well and samples were counted using a TopCount counter (PERKINELMER, Courtaboeuf, France) (Counting yield of 55%). Non-specific binding was measured in the presence of 1 μM AVP. A one-site inhibition mass action curve was fitted to inhibition binding data using Kaleidagraph (SYNERGY SOFTWARE, Reading, Pa., USA). $IC_{50}$ values were converted to $K_i$ for competition experiments using the Cheng-Prusoff equation (Cheng et al., Biochem. Pharmacol., 1973, 22, 3099-3108).

1.2 FLIPR Assays

FLIPR assays were conducted to profile U-Da2a for agonist and antagonist activities on different G protein-coupled-receptors (GPCRs).

Percentage activation and percentage inhibition values were determined on each GPCR. Percentage activation values were determined upon initial addition of 1 μM of U-Da2a. Furthermore, U-Da2a was incubated at 25° C. for 2 min prior to determination of percentage inhibition. Percentage inhibition values were determined upon addition of a reference agonist at an estimated $EC_{80}$ concentration. All wells were prepared using EMD Millipore's GPCRProfiler® Assay Buffer. The GPCRProfiler® Assay Buffer was a modified Hanks Balanced Salt Solution (HBSS) where HBSS was supplemented to contain 20 mM HEPES and 2.5 mM Probenecid at pH7.4. The agonist assay was conducted on a $FLIPR^{TETRA}$ instrument where U-Da2a, vehicle controls, and Emax of the reference agonist were added to the assay plate after a fluorescence baseline was established. The agonist assay was a total of 180 seconds and was used to assess each compound's ability to activate each GPCR assayed. Antagonist Assay was performed using $EC_{80}$ potency values determined previously, all pre-incubated (2 minutes) sample compound wells were challenged with $EC_{80}$ concentration of reference agonist after establishment of a fluorescence baseline. The antagonist assay was conducted using the same assay plate and the same apparatus that was used for the agonist assay. All assay plate data were subjected to appropriate baseline corrections. After baseline corrections were applied, maximum fluorescence values were exported and data processed to calculate percentage activation (relative to Emax reference agonist and vehicle control values), percentage inhibition (relative to $EC_{80}$ and vehicle control values), and additional statistical values (i.e. Z', percentage variation between replicate data values) to assess the quality of each plate. Where assay plate data were rejected, additional experiments were conducted.

1.3 Electrophysiological Assays

Electrophysiological assays to test U-Da2a for activities on cardiac ion channels (Nav1.5, Cav1.2, Kv4.3/KChIP2, Kv1.5, KCNQ1/mink, Kir2.1, hERG, HCN4) were performed with the IonWorks Quattro and IonWorks HT electrophysiological platforms (MOLECULAR DEVICES) according to the manufacturer's instructions. U-Da2a was prepared in water to 300 μM concentration. The stock solution was transferred to a master plate and into assay plates where 2 μl per well of the solution were placed. On the day of the assay, 198 μl of external solution containing the appropriate DMSO concentration was added and mixed thoroughly. This provided a 1:100 dilution. A further 1:3 dilution occurred upon addition to the cells in the IonWorks, giving a 1:300 dilution in total. On each assay plate, at least 8 wells were reserved for vehicle control (0.3% DMSO) and at least 8 wells for each positive control specific to the cell line tested. The positive controls were tested at a maximal blocking and an approximate $IC_{50}$ concentration. The compounds used for positive controls: Nav1.5 100 μM and 5 mM Lidocaine, Kv4.3/KChIP2 20 μM and 500 μM Quinidine, Cav1.2 1 μM and 100 μM Nitrendipine, Kv1.5 300 μM and 10 mM 4-AP, KCNQ1/minK 10 μM and 100 μM Chromanol 293B, hERG 0.1 μM and 1 μM Cisapride, HCN4 50 μM and 3 mM Cesium, Kir2.1 20 μM and 500 μM Barium.

2) Results

Binding tests were performed at the equilibrium on the three vasopressin receptor subtypes using the radio-labeled ligand $^3$H-AVP. U-Da2a has an affinity between 2 and 5 nM for the V2R whereas even at a concentration of 1 μM the toxin did not inhibit the binding of $^3$H-AVP to the V1aR and V1bR (FIG. 2).

FLIPR assays were conducted to profile U-Da2a for agonist and antagonist activities on 157 GPCRs: M1, M2, M3, M4, M5, A1, A2B, A3, alpha1 A, alpha1B, alpha1D (D2-79), alpha2A, beta 1, beta 2, beta 3, C3aR, C5aR, AT1, APJ, BB1, BB2, BB3, Bradykinin B2, CGPR1, CaS, CB1, CB2, ChemR23, CCR1, CCR10, CCR2B, CCR3, CCR4, CCR5 rhesus macaque, CCR6, CCR7, CCR8, CCR9, CX3CR1, CXCR1, CXCR2, CXCR3, CXCR4, CXCR5, CXCR6, XCR1/GPR5, CCK1, CCK2, CRF1, CRF2, D1, D2L, D4, D5, ETA, ETB, GPR41, GPR43, GABAB1b, GAL1, GAL2, Ghrelin Receptor, GLP, GLP-1, GLP-2, glucagon, secretin receptor, mGlu1, mGlu2, TSH, GnRH, H1, H2, H3, GPR99, GPR54, BLT1, CysLT1, CysLT2, LPA1, LPA3, LPA5/GPR92, S1P1, S1P2, S1P3, S1P4, SIP5, MrgD, MRGX1, MRGX2, MCHR1, MCHR2, MC2, MC4, MC5, motilin receptor, NMU1, NMU2, NPBW1 GPR7, Y2, Y4, NTR1, FPR1, FPRL1, GPR109A, Delta, Kappa, Mu, NOP/ORL1, OX1, OX2, GPR39, OT, GPR103/QRFP, P2RY1, P2RY2, P2RY4, P2RY11, P2RY12, PAF, PK1, PK2, PRP, DP, EP1, EP2, EP3, EP4, FP, IP1, TP, Trypsin-activated PARs, Thrombin-activated PARs, PTH1, PTH2,5-HT1A, 5-HT2A, 5-HT2B, 5-HT2C, 5-HT4B, 5-HT6, SST2, SST3, SST4, SST5, GPR68/OGR1, SUCNR1/GPR91, NK1, NK2, NK3, TRH, GPR14, V1A, V1B, V2, PAC1 long isoform, VPAC1 and VPAC2. U-Da2a activity was detected only on V2R, antagonized by 69%, thus demonstrating the selectivity of U-Da2a for the V2R receptor.

Electrophysiological assays were performed to test U-Da2a for activities on cardiac ion channels Nav1.5, Cav1.2, Kv4.3/KChIP2, Kv1.5, KCNQ1/mink, Kir2.1, hERG and HCN4. U-Da2a did not appear to exhibit significant inhibition of any of the ion channels at a concentration of 1 μM. These results demonstrate that U-Da2a has a unique activity on V2R which is different and unexpected from the known activity of dendrotoxins on cardiac ion channels.

Example 3

In Vitro Characterization of U-Da2a Pharmacological Effects

1) Materials and Methods 1.1 Competitive Antagonistic effect on cAMP Production Induced by Activation of the V2R with Vasopressin.

Stably transfected CHO cells expressing the human V2R (Cotte et al., J. Biol. Chem., 1998, 273, 29462-68; Phalipou et al., J. Biol. Chem., 1999, 274, 23316-23327) were plated into 96 wells. 24 hours later the cells were stimulated 24 hours with increasing concentrations of AVP in a 50 μl volume of incubation medium containing DMEM, 5% BSA and 0.1 mM RO 201724 (CALBIOCHEM #557502; MERCK-MILLIPORE), a selective inhibitor of cAMP-specific phosphodiesterase, in the absence (control condition) or in the presence of increasing concentrations of U-Da2a (inhibitory conditions). cAMP measurement was performed using the Homogeneous Time-Resolved Fluorescence Resonance Energy Transfer technology (HTRF®) developed by CISBIO-INTERNATIONAL using the cAMP Dynamic 2 kit (CISBIO-INTERNATIONAL). After 30 min stimulation at 37° C., the cells were lysed by adding 50 μl of lysis buffer to the incubation medium. The lysis buffer contained cAMP labeled with an acceptor fluorophore (cAMP-d2) emitting at 665 nm. Then 50 μl of lysis buffer containing an anti-cAMP antibody labeled with a donor fluorophore (Anti-cAMP Europium Kryptate=AC-K) emitting at 620 nm were added. In the absence of endogenous cAMP, the FRET ratio 665/620 is maximal between cAMP-d2 and AC-K. As soon as endogenous cAMP is produced by cells after stimulation, it competes with cAMP-d2 and the ratio 665/620 decreases. The endogenous cAMP concentration is determined by comparison between the experimental 665/620 ratio and a standard curve established with known cAMP concentrations. These measurements are performed on a laser-based HTRF® reader Rubystar with Rubystar software (BMG LABTECH).

1.2 Competitive Antagonist Effect of the Toxin U-Da2a on β-Arrestin-1 Mobilization after V2R Activation by Vasopressin 2.5×10$^6$ tsA cells, a transformed human kidney (HEK293) cell line stably expressing an SV40 temperature sensitive T antigen (ECACC), transiently transfected with 150 ng of pRK5 expression plasmid for hV2Rluc (PHARMINGEN #556104, BD BIOSCIENCE; Terrillon et al., Mol. Endocrinol., 2003, 17, 677-691) and with 1 μg of an expression plasmid for β-arrestin-1-YFP ((β-arrestin cloned into pEYFP-N1 (CLONTECH); Scott et al., J. Biol. Chem., 2002, 277, 3552-3559) were seeded in 6-well plates. 48 h after transfection, cells were washed with KREBS buffer containing 146 mM NaCl, 4.2 mM KCl, 0.5 mM $MgCl_2$, 1 mM $CaCl_2$, 10 mM HEPES pH 7.4, 1 mg/ml glucose and resuspended in 1 ml of this buffer. Bioluminescence Resonance Energy Transfer (BRET™) measurements between the V2-Rluc and β-arrestin-1-YFP were performed in 96-well plates with a final volume of 50 μl containing 30 μl of cell suspension (75,000 cells), 10 μl of KREBS buffer (control condition) or the mix of ligands containing either increasing concentrations of vasopressin (stimulated control condition) or in the presence of increasing concentrations of toxin (stimulated condition with inhibitor). 10 μl of Coelenterazine h (Renilla luciferin; MOLECULAR PROBES C-6780, INVITROGEN, LIFE TECHNOLOGIES), the luciferase substrate, was then added to the mix and incubated at 37° C. before BRET measurements were be performed in a microplate luminometer (Mithras LB940 BERTHOLD TECHNOLOGIES) using MikroWin 2000 software (MIKROTEK LABORSYSTEME, GmbH).

1.3 Competitive Antagonist Effect of the Toxin U-Da2a on MAP Kinase Phosphorylation after V2R Activation by AVP 10×10$^6$ tsA cells, a transformed human kidney (HEK293) cell line stably expressing an SV40 temperature sensitive T antigen (ECACC), transiently transfected with 500 ng of pRK5 expression plasmid for human V2R (PHARMINGEN #556104, BD BIOSCIENCE; Terrillon et al., Mol. Endocrinol., 2003, 17, 677-691) were plated into poly-ornithin-coated 96-well plates with 75,000 cells per well with DMEM medium containing 10% serum. Eight hours and twenty-four hours later, the cells were starved with serum-free medium and stimulated another twenty-seven hours later. Transfected cells were incubated for 10 min at 37° C. with DMEM (control condition) or with increasing doses of AVP (stimulated condition) or with a mix of AVP and toxin (stimulated condition with inhibitor). Then the medium was replaced with 50 μl of lysis buffer from the Cellul'ERK kit (CISBIO INTERNATIONAL) and the cells were incubated for 30 min at room temperature. In a 384 well plate, to 16 μl of lysed cells first 2 μl of the antibody against phosphorylated ERK labeled with acceptor fluorophore (AC-ERK-P-d2 emitting at 665 nm) and then 2 μl of the antibody against total ERK labeled with donor fluorophore (AC-ERK-K emiting at 620 nm) were added. When ERK phosphorylation occurs, the acceptor in close vicinity of the donor is able to emit at 665 nm producing the FRET signal. The increase in the 665/620 ratio corresponds to the increase in MAP kinase phosphorylation. Two hours later, RT-FRET was measured on a laser-based HTRF® reader Rubystar with Rubystar software (BMG LABTECH).

2) Results

Figure 3:
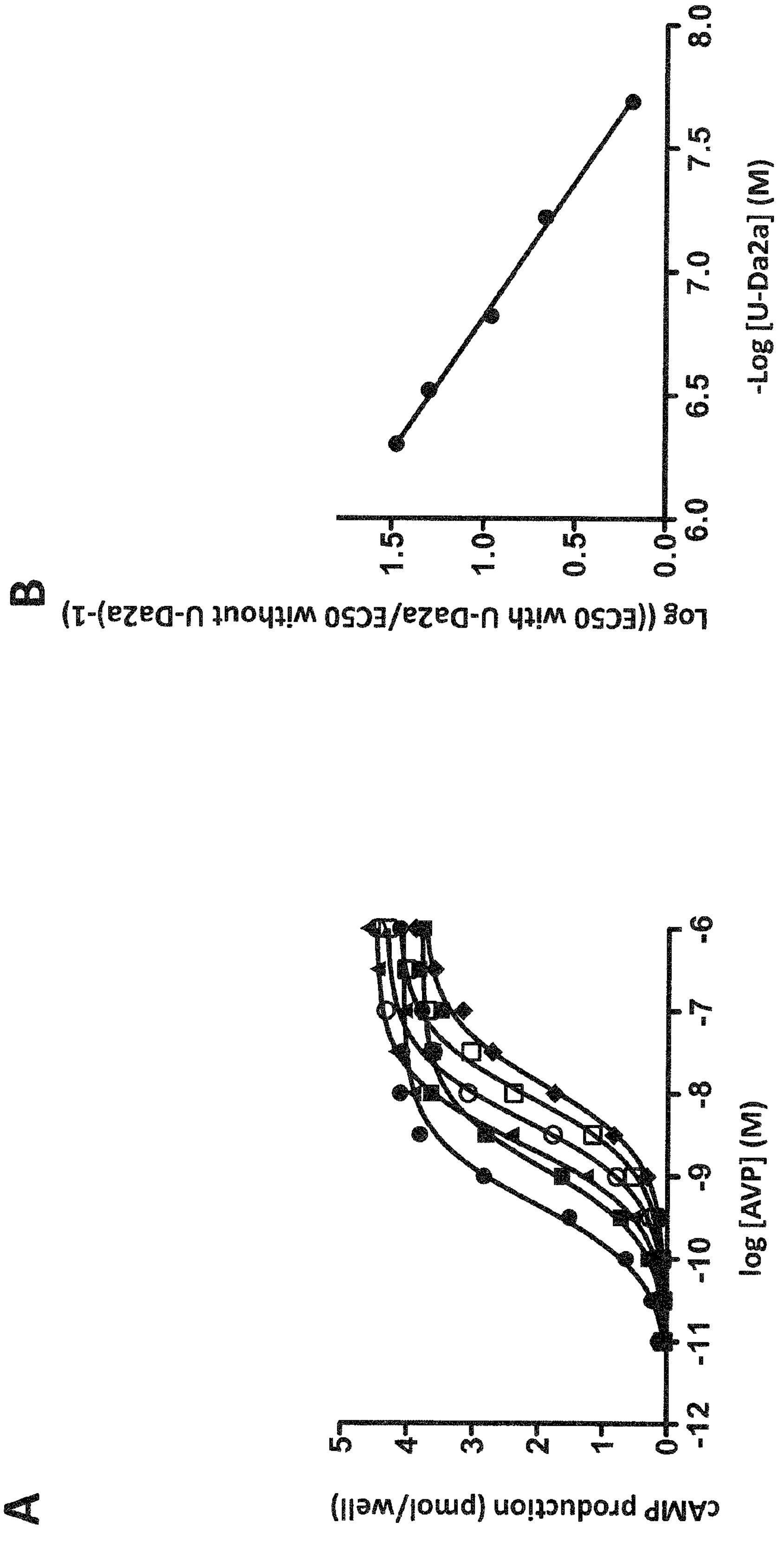
FIG. 3 illustrates U-Da2a toxin effects on cAMP production induced by AVP on CHO cells stably expressing human V2R. A. Dose-response curves induced by AVP on the V2R in the absence (●) or in the presence of increasing U-Da2a concentrations: 20 nM (■); 60 nM (▲); 150 nM (○); 300 nM (□) and 500 nM (♦). B. Schild representation of U-Da2a toxin effects on cAMP production induced by increasing AVP concentrations on the V2R. These cumulative data are obtained from 3 independent experiments.
Figure 4:
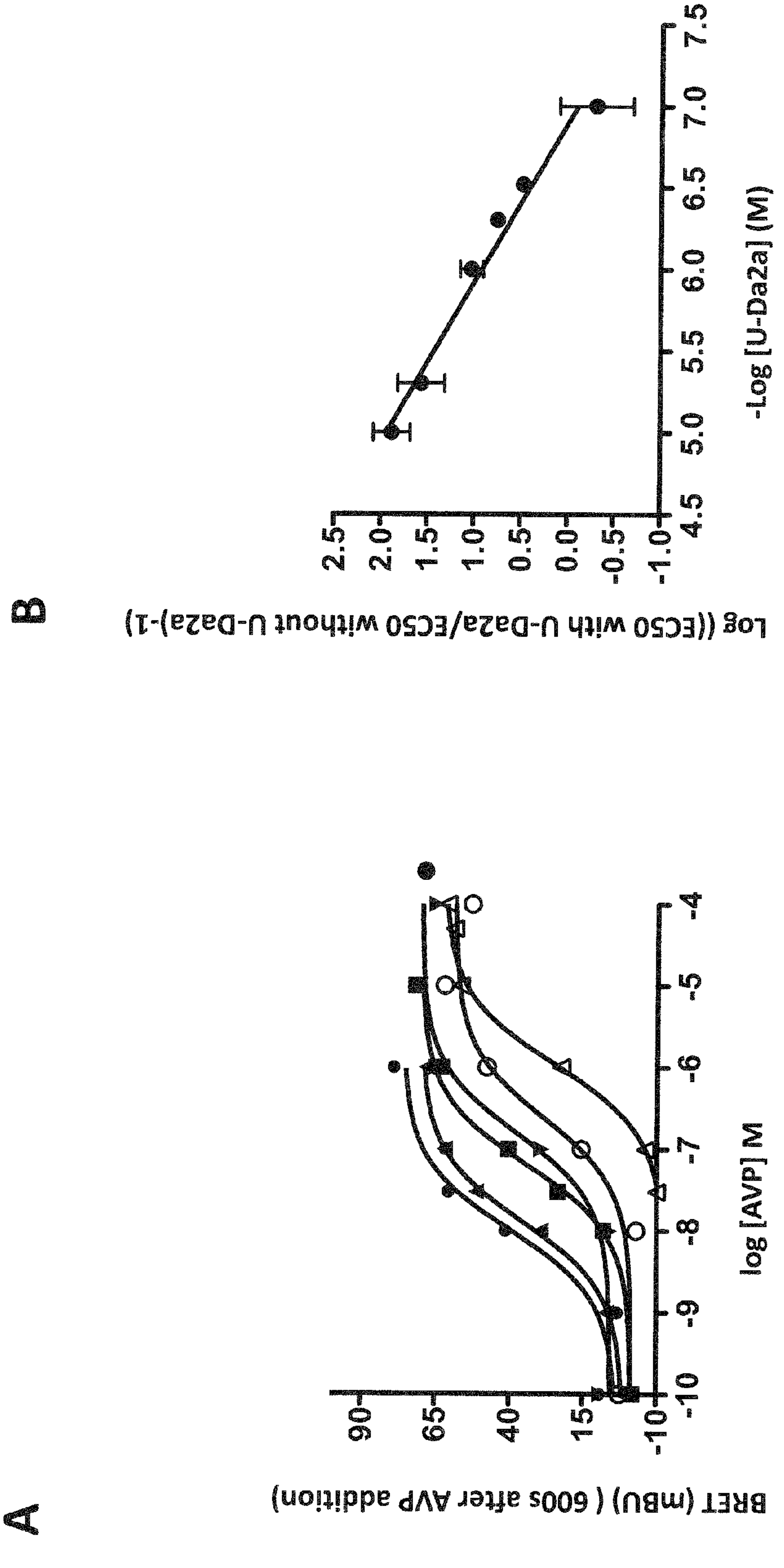
FIG. 4 illustrates U-Da2a effect on β-arrestin-1-YFP mobilization induced by the action of AVP on the V2R-Rluc receptor in tsA cells. A. AVP dose-responses curves on the V2R in the absence (●) or in the presence of increasing concentrations of U-Da2a: 100 nM (▲); 500 nM (■); 1 μM (▼); 5 μM (○) and 10 μM (Δ). B. Schild representation of U-Da2a toxin effects on β-arrestin-1-YFP mobilization to the V2-Rluc receptor induced by increasing AVP concentrations. These cumulative data are obtained from 3 independent experiments.
Figure 5:
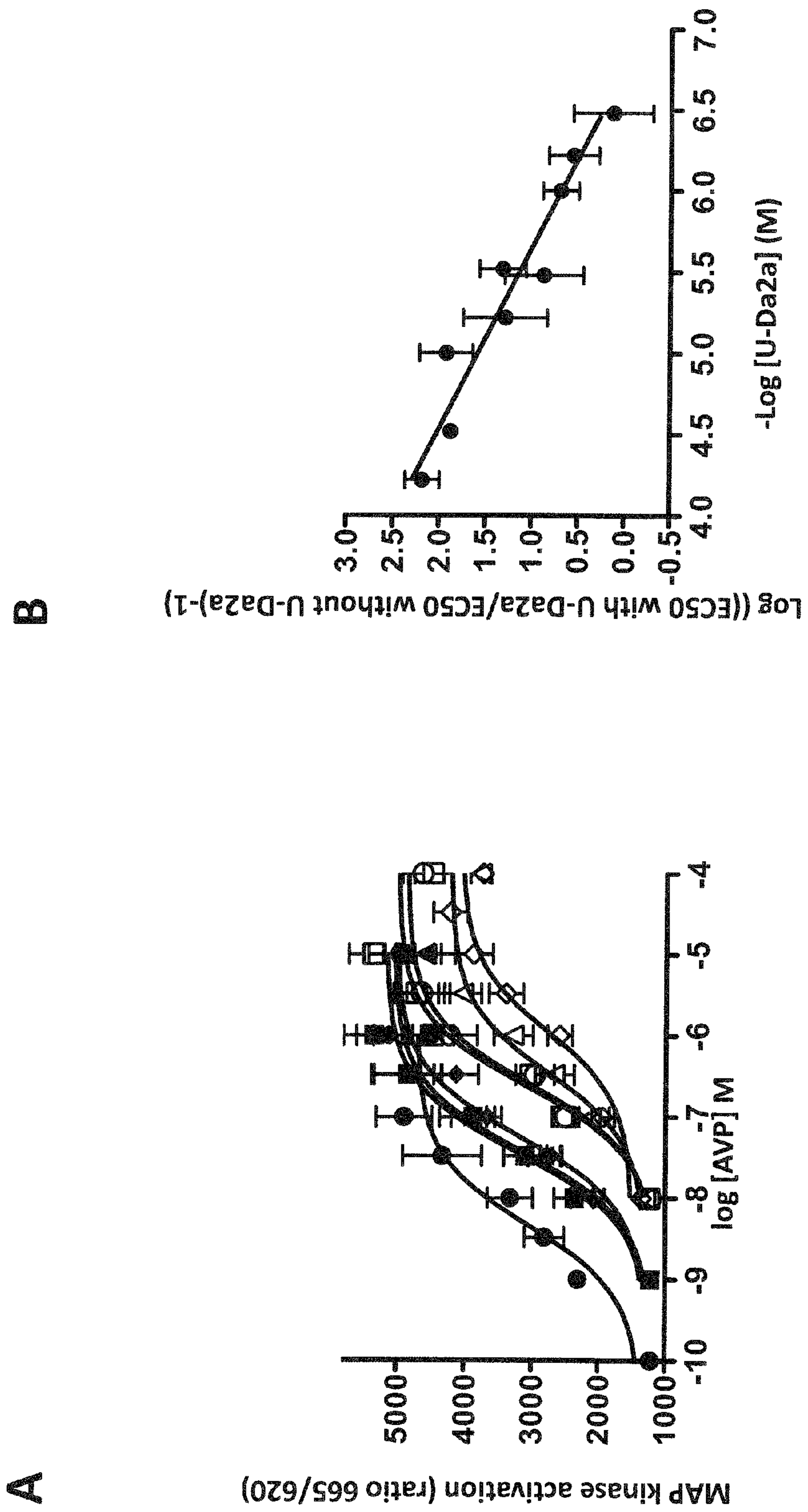
FIG. 5 illustrates UDa-2a effect on MAP kinase phosphorylation induced by the action of AVP on the V2R in tsA cells. A. AVP dose-responses curves on the V2R in the absence (●) or in the presence of increasing concentrations of U-Da2a: 0.6 μM (■); 1 μM (▲); 3 μM (♦); 6 μM (○); 10 μM ((□); 30 μM (Δ) and 60 μM (◇). B. Schild representation of U-Da2a toxin effects on MAP kinase phosphorylation induced by increasing AVP concentrations to the V2R receptor. These cumulative data are obtained from 3 independent experiments.

In vitro characterization of U-Da2a pharmacological effects demonstrate that U-Da2a is able to inhibit cAMP production induced by V2R activation in a competitive manner with a shild coefficient of −0.91±0.02, a $K_{inact}$ of 12.0±0.4 nM and a PA2 of 7.92±0.02 (FIGS. 3A and 3B). U-Da2a is also able to inhibit β-arrestin-1-YFP mobilization on the hV2-Rluc receptor in a competitive way with a shild coefficient of −0.9±0.2 and a $K_{inact}$ of 110±50 nM and a PA2 of 7.0±0.2 (FIGS. 4A and 4B). Finally, U-Da2a is able to inhibit MAP kinase phosphorylation following AVP stimulation of the V2R in a competitive way with a shild coefficient of −0.9±0.2 and a $K_{inact}$ of 210±80 nM and a PA2 of 6.9±0.2 (FIGS. 5A and 5B). These functional cellular assays have demonstrated the competitive antagonist properties of U-Da2a towards the three major signaling pathways of the V2R, i.e., cAMP accumulation, arrestin recruitment and MAP kinase phosphorylation.

Example 4

In Vivo Characterization of the Pharmacological Effects of U-Da2a

1) Materials and Methods 1.1 Dose-Response Experiment

The toxin was dissolved in 0.9% NaCl at a concentration of 1 mg/ml. Adult CD1$^{pcy/pcy}$ (Takahashi et al., J. Urol., 1986, 135, 1280-1283, and J. Am. Soc. Nephrol., 1991, 1, 980-989 and Olbrich et al., Nature Genetics, 2003, 34, 455-459) and adult C57BL/6 mice were injected intraperitoneally and subcutaneously with the toxin at doses of 1, 0.1 and 0.01 μmol toxin/kg of body weight. One, three and five days after the first injection the mice were kept for 24 hours in metabolic cages. The collected urine was centrifuged for 30 minutes at 14,000 rpm. Urine osmolality (mOs/kg) was determined with a Knauer osmometer, urine volume (μl) was measured with a pipette.

1.2 Long-Term Administration Experiment

The toxin was dissolved in 0.9% NaCl at a concentration of 1 mg/ml and administered intraperitoneally to adult CD1$^{pcy/pcy}$ mice at a dose of 0.1 μmol/kg/day. At 0, 30 70 and 99 days, urine was collected for 24 hours in metabolic cages and urine volume and urine osmolarity were determined.

2) Results

The effect of the toxin in vivo was tested in the CD1$^{pcy/pcy}$ mouse line, an animal model of polycystic kidney disease, in which V2R antagonists were previously shown to inhibit cyst formation. Since U-Da2a is a specific, selective and bioavailable antagonist of V2R which inhibits the three signaling pathways of the V2R, this toxin represents a valuable therapeutic drug against polycystic kidney disease.

Figure 6:
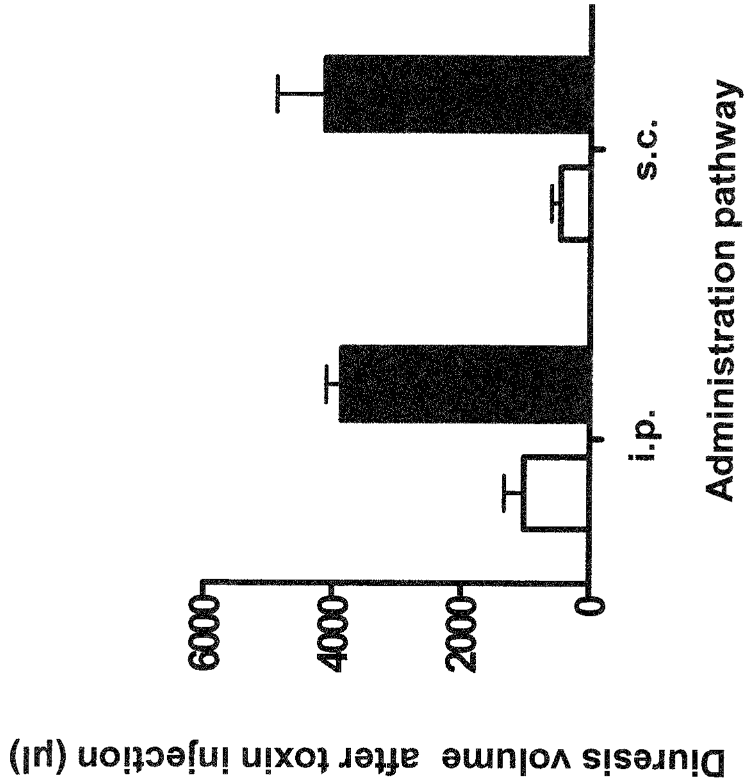
FIG. 6 illustrates the diuretic effect of U-Da2a toxin in $CD1^{pcy/pcy}$ mice. U-Da2a was injected subcutaneously and intraperitoneally to $CD1^{pcy/pcy}$ mice at a single dose of 1 μmol/kg. Following injection, urine was collected for 24 hours in metabolic cages and urine volume was determined. urine volume in the basal state (empty box) and after U-Da2a injection (black box).
Figure 7:
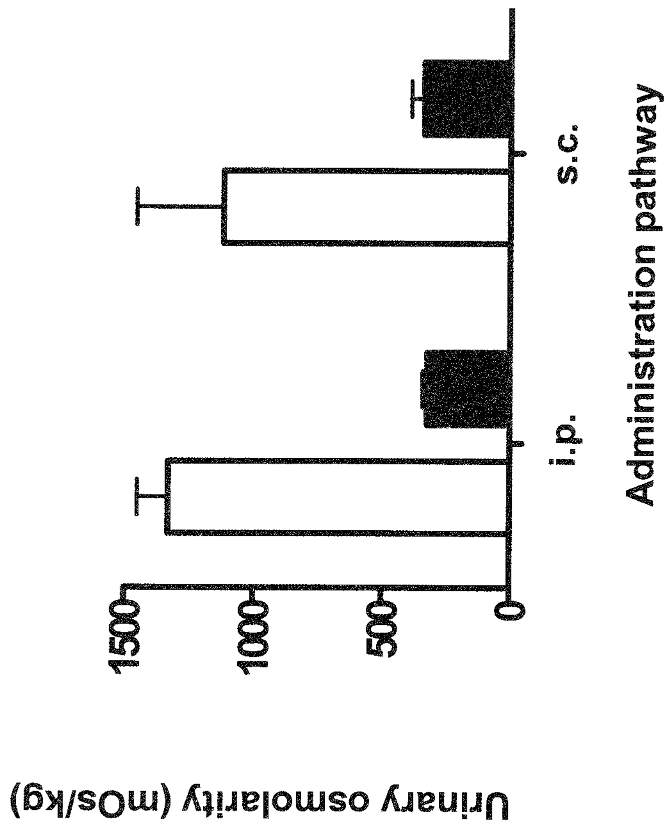
FIG. 7 illustrates the osmolarity effect of U-Da2a toxin in $CD1^{pcy/pcy}$ mice. U-Da2a was injected subcutaneously and intraperitoneally to $CD1^{pcy/pcy}$ mice at a single dose of 1 μmol/kg. Following injection, urine was collected for 24 hours in metabolic cages and urine osmolarity was measured. Basal state (empty box). U-Da2a (black box).

In a first set of experiments, the toxin was administered intraperitoneally and subcutaneously to CD1$^{pcy/pcy}$ mouse, at a single dose of 0.1 μmol/kg. Urine volume for CD1$^{pcy/pcy}$ mice at basal state is very low with a high osmolarity. On the contrary, i.p. or s.c. U-Da2a injection at 1 μmol/kg leads to a strong increase in urine volume due to the antagonist effect of the toxin on the V2R leading to a diuretic effect (FIG. 6). The diuretic effect was correlated with a strong decrease in osmolarity (FIG. 7), i.e., a decrease in salt concentration, due to the increase in urine volume. These results demonstrate that U-Da2a is able to reach its target in vivo, the V2R either subcutaneouly or intraperitoneally. For technical reasons, the well tolerated intraperitoneal pathway was used in the next tests.

Figure 8:
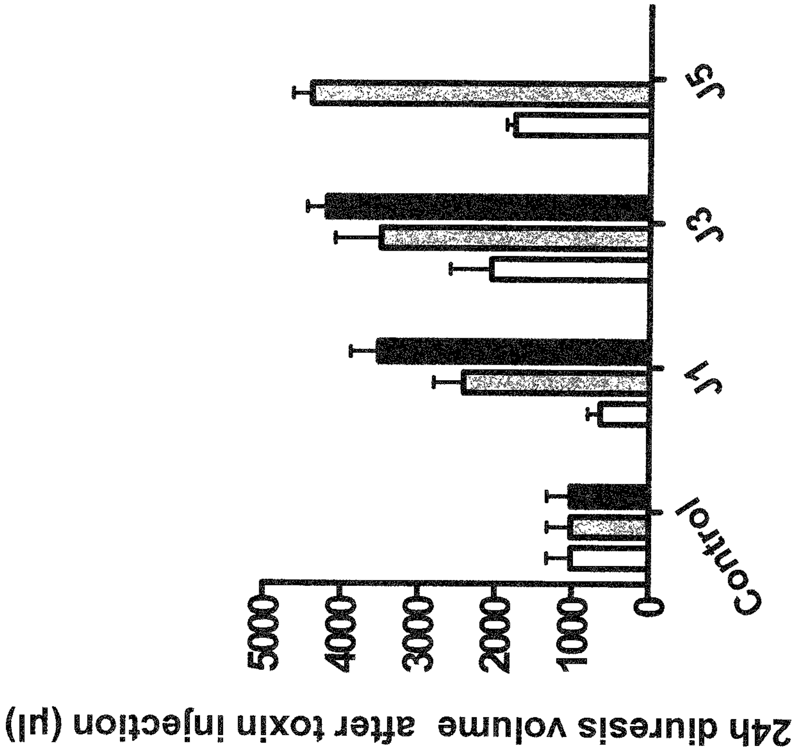
FIG. 8 illustrates the diuretic effect of increasing U-Da2a toxin doses by intraperitoneal administration in $CD1^{pcy/pcy}$ mice. U-Da2a was injected intraperitoneally to $CD1^{pcy/pcy}$ mice at doses of 0.01 (empty box), 0.1 (grey box) and 1 (black box) μmole/kg at 1, 3 and 5 days. Urine was collected for 24 hours following injection, in metabolic cages and urine volume was determined.
Figure 9:
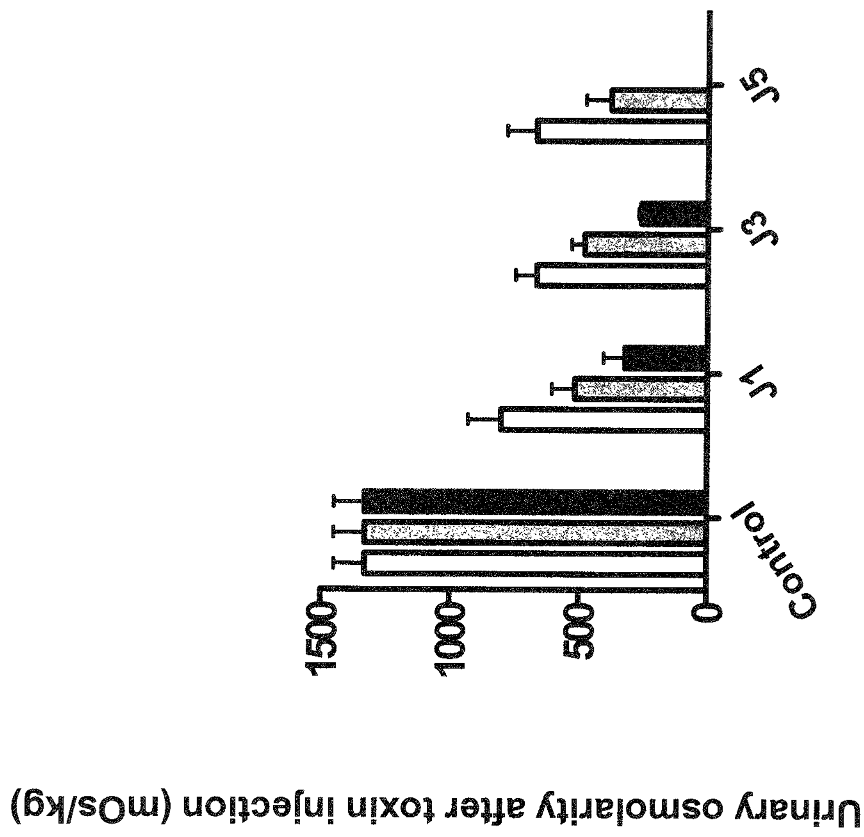
FIG. 9 illustrates the osmolarity effect of increasing U-Da2a toxin doses by intraperitoneal administration in $CD1^{pcy/pcy}$ mice. U-Da2a was injected intraperitoneally to $CD1^{pcy/pcy}$ mice at doses of 0.01 (empty box), 0.1(grey box) and 1 (black box) μmole/kg at 1, 3 and 5 days. Urine was collected for 24 hours following injection, in metabolic cages and urine volume was determined.

In a second set of experiments, the toxin was administered intraperitoneally to CD1$^{pcy/pcy}$ mice, at doses of 1, 0.1 and 0.01 μmol toxin/kg of body weight. A dose-dependent diuretic effect and a decrease in urine osmolarity were observed after injection of the toxin (FIGS. 8 and 9, respectively). A dose of 0.1 μmol/kg is sufficient to observe the maximal effect of the toxin.

Figure 10:
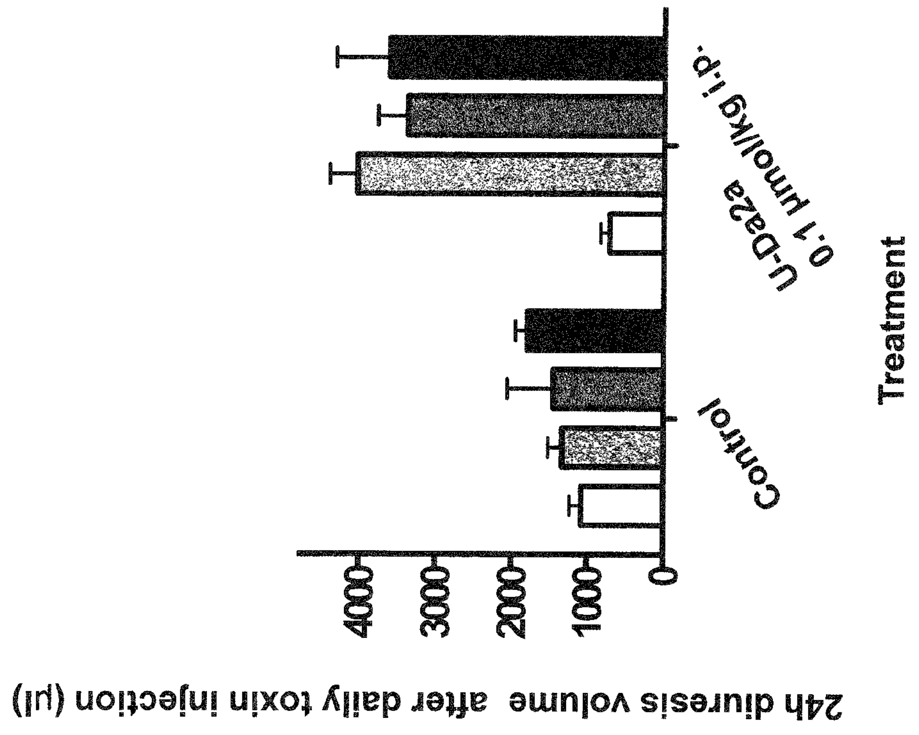
FIG. 10 illustrates the diuretic effect of U-Da2a in $CD1^{pcy/pcy}$ mice after daily i.p. injections of U-Da2a at 0.1 μmol/kg for up to 99 days. At 0 (empty box), 30 (light grey box), 70 (dark grey box) and 99 (black box) days, urine was collected for 24 hours in metabolic cages and urine volume was determined.
Figure 11:
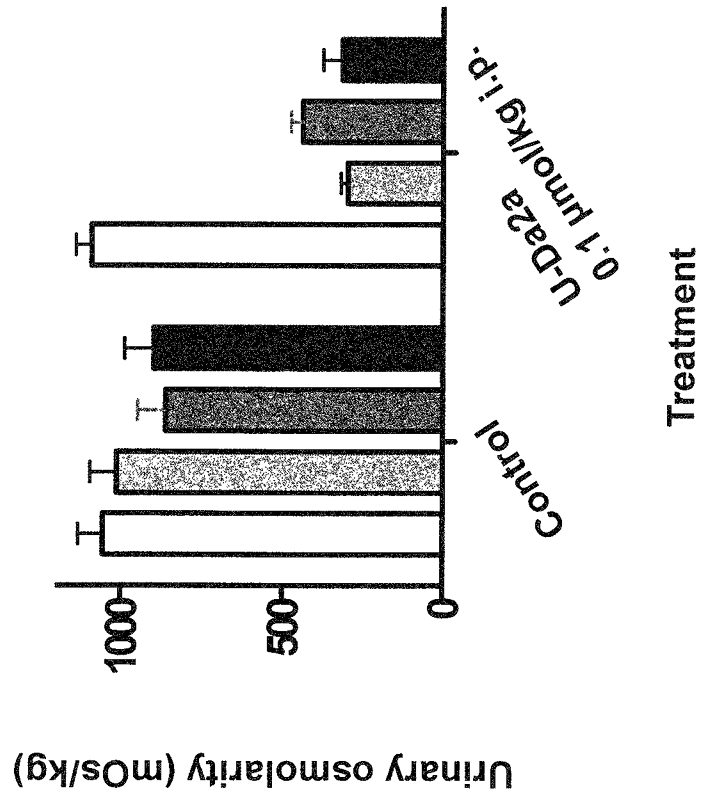
FIG. 11 illustrates the osmolarity effect of U-Da2a in $CD1^{pcy/pcy}$ mice after daily i.p. injections of U-Da2a at 0.1 μmol/kg for up to 99 days. At 0 (empty box), 30 (light grey box), 70 (dark grey box) and 99 (black box) days, urine was collected for 24 hours in metabolic cages and urine osmolarity was determined.

In a third set of experiments, the toxin was administered at a dose of 0.1 μmol/kg/day for 99 days. Urine volume and urine osmolarity were determined at 0, 30, 70 and 99 days (FIGS. 10 and 11, respectively). No toxic effect was detectable after long-term daily injections of the toxin (99 days).

Example 5

Clinical Trial for Testing U-Da2a Efficiency as a Therapeutic Agent Against Cyst Formation in Pcy Mice 1) Materials and Methods The toxin was dissolved in 0.9% NaCl at a concentration of 1 mg/ml. 10 week-old CD1$^{pcy/pcy}$ mice were injected intraperitoneally with the toxin at a dose of 0.1 μmol toxin/kg of body weightday for 99 days. Then the mice were perfusion-fixed with 4% paraformaldehyde/1× phosphate-buffered saline, the kidneys and hearts were taken out and weighed. Then, the ratio of kidney weight or heart weight-body weight and kidney weightheart weight was calculated to evaluate an effect of the toxin on cyst formation. The kidneys were embedded in paraffin. Transverse kidney sections were stained with hematoxylin and eosin. Cyst number was determined using the program ImageJ and related to the size of the section thus arriving at the relative cyst number.

2) Results

Figure 12:
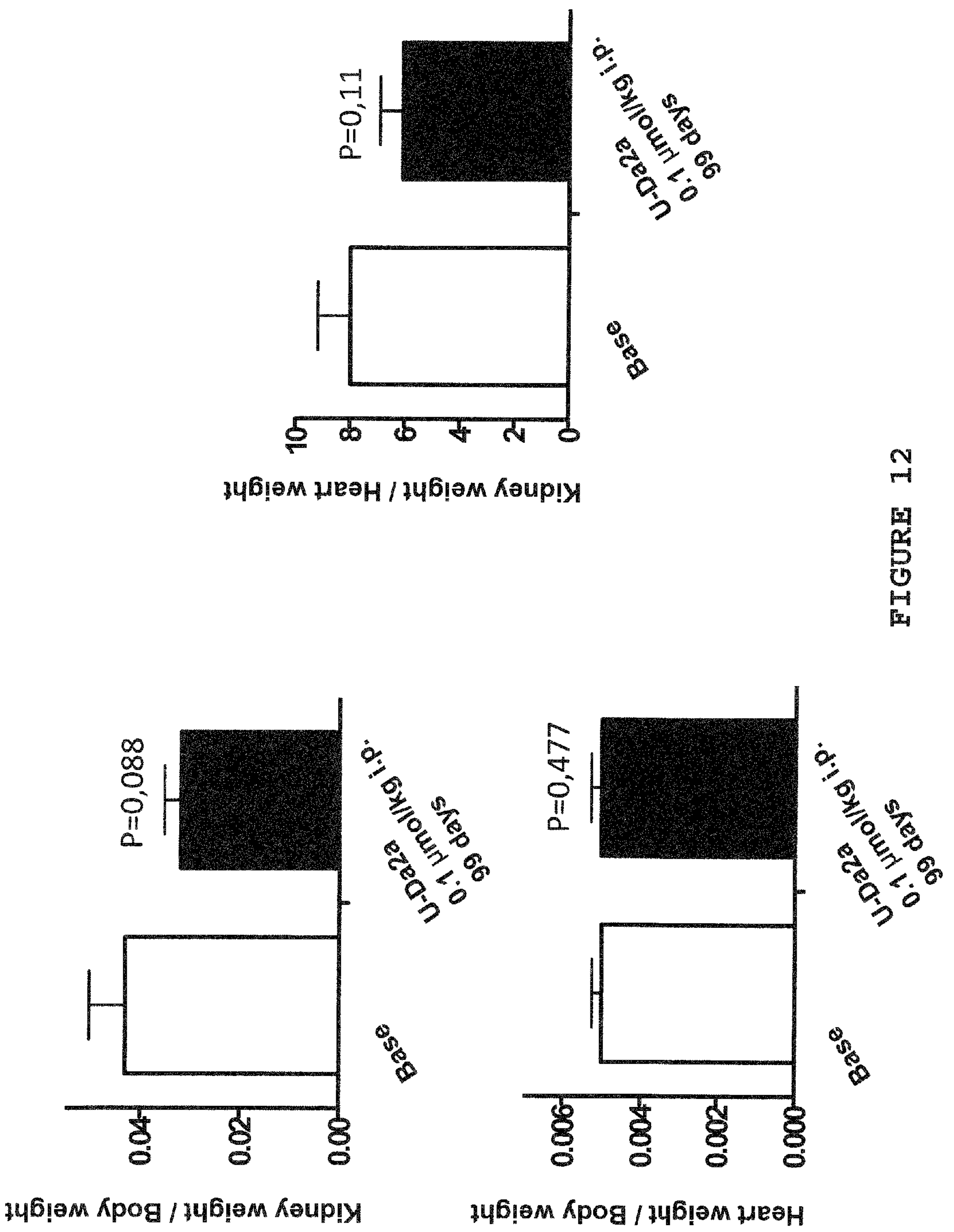
FIG. 12 illustrates the effect of U-Da2a on kidney weight in $CD1^{pcy/pcy}$ mice after 99 days of daily toxin injections at 0.1 μmol/kg i.p. by representing the ratios of kidney weight-body weight, kidney weightheart weight and heart weight-body weight. The mice were perfusion-fixed with 4% paraformaldehyde/1× phosphate-buffered saline, the kidneys and hearts were taken out and weighed. Basal state (empty box). U-Da2a (black box).

The administration of U-Da2a at a dose of 0.1 μmol/kg reduces kidney weight in CD1$^{pcy/pcy}$ (FIG. 12). In addition, histological analysis of the kidney demonstrates that treatment with U-Da2a significantly reduces the number of cysts (FIG. 13).

Example 6

Determination of U-Da2a Amino Acid residues Involved in V2R Antagonist Activity 1) Materials and Methods The proteins were prepared using the protocols described for U-D2a in example 1 and V2R binding assays were performed as described in example 2.

2) Results

Competition binding assays were performed on the following U-Da2a variants and known dendrotoxins:

an U-Da2a variant having an N-terminal deletion of 4 amino acid residues (U-Da2a-delta4 N-ter, SEQ ID NO: 11), an U-Da2a variant having an N-terminal deletion of 2 amino acid residues and a C-terminal deletion of 2 amino acid residues (U-Da2a-delta2 N-ter/delta2 C-ter, SEQ ID NO: 12)

an U-Da2a variant having the substitution S3K (U-Da2a-S3K, SEQ ID NO: 15), an U-Da2a variant having the substitutions N15K/G16A (U-Da2a-N15K, G16A, SEQ ID NO: 14), Dtx-B A27S (SEQ ID NO: 3)

Dtx-K (SEQ ID NO: 8),

DtxE R55 (SEQ ID NO: 7), and.

an U-Da2a variant having the substitutions C14S and C38S (SEQ ID NO: 16).

Figure 14:
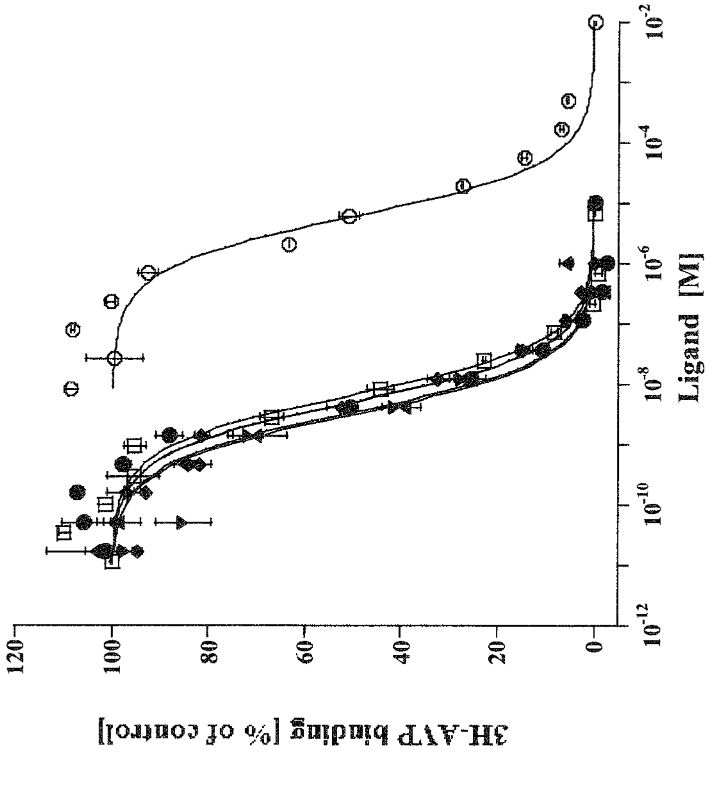
FIG. 14 illustrates $^{3}$H-AVP binding inhibition by U-Da2a and U-Da2a variants on the vasopressin V2 receptor subtype (V2R) expressed in eukaryotic cells. (●) AVP. (▲) U-Da2a WT. (□) U-Da2a-delta4-Nter. (♦) U-Da2a-delta2-Nter-delta2-Cter. (▼) U-Da2a-S3K. (○) U-Da2a-N15K, G1 6A.

The results demonstrate that the N-terminal and C-terminal regions of U-Da2a are not required for binding V2R and blocking its activity by inhibiting the binding of its natural ligand AVP since U-Da2a variants having N- and/or C-terminal deletions or substitutions in the N-terminal region display similar affinity on V2R than U-Da2a (FIG. 14 and Table I).

By contrast, the residues N15 and G16 which are at positions homologous to those of the active site of the basic pancreatic trypsin inhibitor (BPTI) but correspond to different amino acids (N15, G16 for U-Da2a versus K15 and A16 in BPTI) are essential for binding V2R and inhibiting its activity since the U-Da2a variant with the NG residues in positions 15 and 16 replaced by the residues K and A display a 1000-fold less affinity for V2R (FIG. 14 and Table I).

TABLE I

| Binding affinity of the ligands for V2R | |
|---|---|
| Ligand | Ki (nM ± SEM) |
| AVP | 1.44 ± 0.69 |
| U-Da2a-WT | 1.03 ± 0.34 |

TABLE I-continued

| Binding affinity of the ligands for V2R | |
|---|---|
| Ligand | Ki (nM ± SEM) |
| U-Da2a-delta4 N-ter | 1.57 ± 1.20 |
| U-Da2a-delta2 N-ter/delta2 C-ter | 3.23 ± 2.31 |
| U-Da2a-S3K | 1.29 ± 0.34 |
| U-Da2a- N15K, G16A | 8030 ± 1300 |

Figure 15:
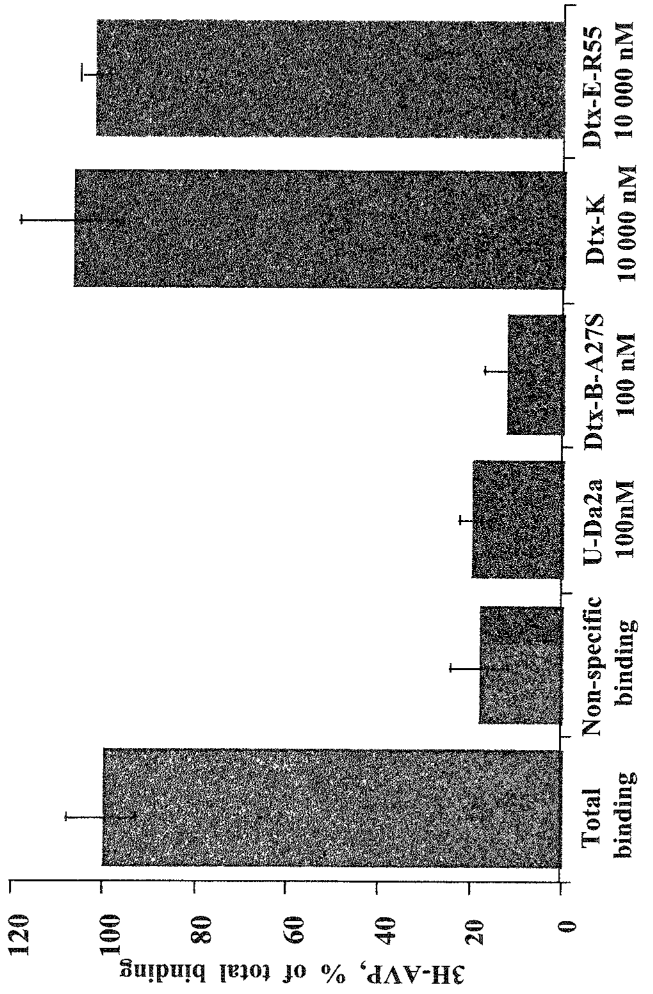
FIG. 15 illustrates $^{3}$H-AVP binding inhibition by U-Da2a, Dtx-B-A27S, Dtx-K, DTx-E-R55 on the vasopressin V2 receptor subtype (V2R) expressed in eukaryotic cells.

These results were confirmed by the binding assays with dendrotoxins having different residues in positions 15 and 16 showing that DTx-E-R55 which has K and A in positions 15 and 16, like BPTI, is not able to block V2R, even at concentrations 100 times higher to those required to obtain a 80% inhibition with U-D2a (FIG. 15). Similarly, no V2R inhibition was obtained with DTx-K which has K and R in positions 15 and 16. By contrast, Dtx-B A275 which has M and F in positions 15 and 16 has V2R inhibiting capacities similar to those of U-D2a (FIG. 15).

These results indicate that U-Da2a pharmacophore is in a position homologous to that of the active site of BPTI, in the loop located in the part of the toxin opposite to the one defined by the N and C-terminal regions. V2R antagonist activity requires NG or MF in positions 15 and 16.

The importance of disulfide bridges in U-Da2a activity was tested with the variant U-Da2a C14S, C38S, which lacks the second disulfide bond (between C2 and C4). This disulfide bond was removed in regard of the existence of the unique Kunitz fold toxin possessing only 2 disulfide bridges, the Conkunitzin-S1 (Accession number UniProtKBSwiss-Prot P0C1X2; SEQ ID NO: 17). This toxin lacks the $2^{nd}$ bridge but adopts the canonical 3(10)-beta-beta-alpha Kunitz fold and displays an activity on potassium channel (Buczek et al., Acta Crystallogr D Biol Crystallogr., 2006, 62, 980-90).

Figure 16:
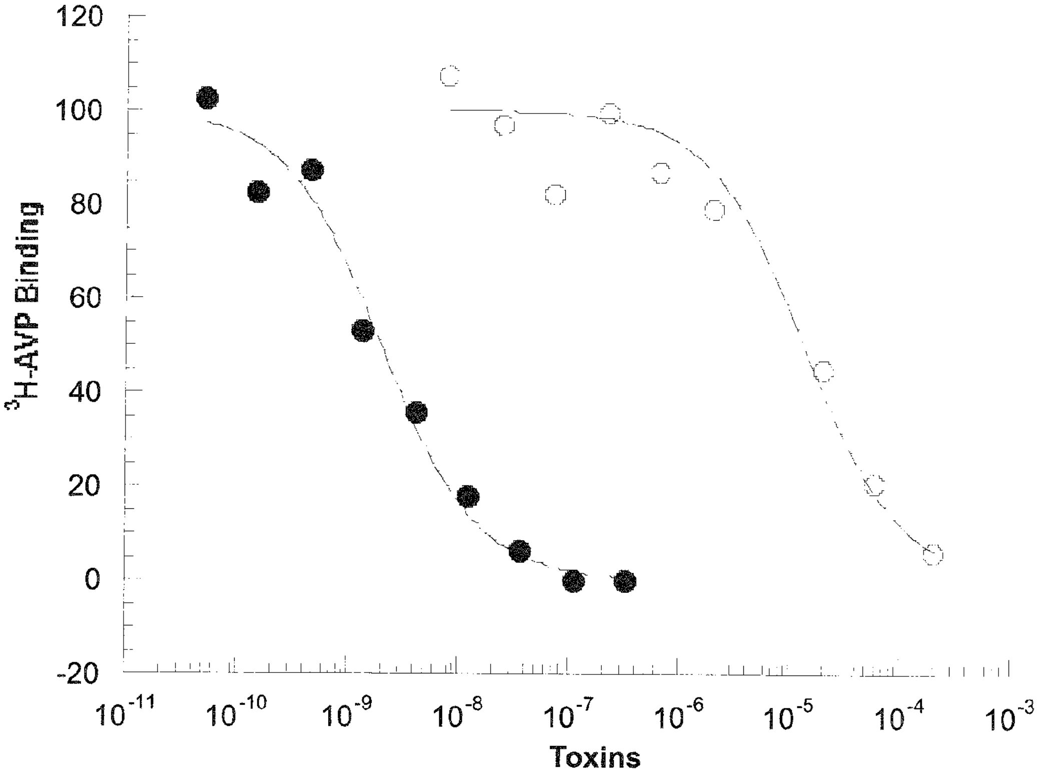
FIG. 16 illustrates binding inhibition of $^{3}$H-AVP on V2R by U-Da2a WT (open circle) and U-Da2a C14S,C38S (full circle). K, U-Da2a WT=1.03 nM. $K_i$ U-Da2a C14S, C38S=6200 nM

Binding assays on V2R shows that the K, of the wild-type U-Da2a is equal to 1.03 nM, whereas that of the C14S,C38S variant is equal to 6200 nM (FIG. 16). These results show that the V2R antagonist activity of the protein of the invention is improved when 3 disulfide bonds (between C1 and C6, C2 and C4 and C3 and C5) are present in the protein.

The invention claimed is:

1. A method of inhibiting the vasopressin-2 receptor (V2R) pathway in a subject in need thereof comprising administering a V2R antagonist to the subject, wherein said V2R antagonist comprises a isolated protein, comprising an amino acid sequence which is at least 65% identical to residues 1 to 57 of SEQ ID NO: 1, and which comprises:

(i) a motif $X_1X_2X_3X_4$ in positions 15 to 18 of SEQ ID NO: 1, wherein $X_1$ is an asparagine (N), $X_2$ is a glycine (G), $X_3$ and $X_4$ are hydrophobic amino acids or $X_1$ is a methionine (M), $X_2$ and $X_3$ are phenylalanines (F), and $X_4$ is an Isoleucine (I), and (ii) one to three disulfide bonds between two cysteine residues, and wherein said V2R antagonist is administered to the subject in an amount sufficient to inhibit the V2R pathway.

2. The method according to claim 1, wherein said protein comprises or consists of a sequence selected from the group consisting of: the amino acid sequences of SEQ ID NO: 1 to 5, a variant of any one of SEQ ID NO: 1 to 3 comprising an N-terminal deletion of one to four amino acid residues and/or a C-terminal deletion of one or two amino acid residues, and a variant of SEQ ID NO: 5 or 6 comprising an N-terminal deletion of one to thirty amino acid residues and/or a C-terminal deletion of one or two amino acid residues.

3. The method according to claim 1, wherein said subject suffers from a disease selected from the group consisting of pathological conditions characterized by euvolemic or hypovolemic hyponatremia, Nephrogenic Syndrome of Inappropriate Antidiuresis, Congenital Nephrogenic Diabetes Insipidus, Polycystic kidney disease, cancers, thrombosis, and Menière disease.

4. An isolated protein, comprising an amino acid sequence which is at least 70% identical to residues 1 to 57 of SEQ ID NO: 1, and which comprises:

(i) a motif $X_1X_2X_3X_4$ in positions 15 to 18 of SEQ ID NO: 1, wherein $X_1$ is an asparagine (N), $X_2$ is a glycine (G), $X_3$ and $X_4$ are hydrophobic amino acids, and (ii) one to three disulfide bonds between two cysteine residues, and wherein said protein has V2R antagonist activity.

5. The protein according to claim 4, wherein said sequence comprises an N-terminal deletion of one to four amino acid residues of SEQ ID NO: 1 and/or a C-terminal deletion of one or two amino acid residues of SEQ ID NO: 1.

6. The protein according to claim 4, wherein said sequence comprises one to three disulfide bonds chosen from disulfide bonds between C1 and C6, C2 and C4, and C3 and C5, wherein C1 to C6 are each a cysteine residue, numbered, respectively from the N-terminus to the C-terminus of said sequence.

7. The protein according to claim 6, wherein C1 to C6 are in positions 5, 14, 30, 38, 51 and 55, respectively of SEQ ID NO: 1.

8. The protein according to claim 4, which comprises or consists of any one of SEQ ID NO: 1 and 11 to 13.

9. The protein according to claim 4, wherein said protein is labeled.

10. An expression vector comprising a polynucleotide encoding a protein according to claim 4.

11. A host cell modified with a polynucleotide encoding a protein according to claim 4.

12. A pharmaceutical composition, comprising at least: (i) a protein according to claim 4, a polynucleotide encoding said protein, and/or a vector comprising said polynucleotide, and (ii) a pharmaceutically acceptable carrier.

13. A diagnostic or imaging reagent comprising a labeled protein according to claim 9.

* * * * *

UNITED STATES PATENT AND TRADEMARK OFFICE

CERTIFICATE OF CORRECTION

PATENT NO. : 9,631,001 B2
APPLICATION NO. : 14/427733
DATED : April 25, 2017
INVENTOR(S) : Nicolas Gilles et al.

It is certified that error appears in the above-identified patent and that said Letters Patent is hereby corrected as shown below:

On the Title Page

"(73) Assignees: COMMISSARIAT A L'ENERGIE ATOMIQUE ET AUX ENERGIES ALTERNATIVES, Paris (FR);
CENTRE NATIONAL DE LA RECHERCHE SCIENTIFIQUE, Paris (FR);
INSTITUT NATIONAL DE LA SANTE ET DE LA RECHERCHE MEDICALE (INSERM), Paris (FR);
UNIVERSITY OF REGENSBURG, Regensburg (DE);
UNIVERSITY DE LIEGE, Liege (BE)"

Should read:

--(73) Assignees: COMMISSARIAT A L'ENERGIE ATOMIQUE ET AUX ENERGIES ALTERNATIVES, Paris (FR);
CENTRE NATIONAL DE LA RECHERCHE SCIENTIFIQUE, Paris (FR);
INSTITUT NATIONAL DE LA SANTE ET DE LA RECHERCHE MEDICALE (INSERM), Paris (FR);
UNIVERSITY OF REGENSBURG, Regensburg (DE);
UNIVERSITE DE LIEGE, Liege (BE)--

Signed and Sealed this
First Day of August, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 17

<210> SEQ ID NO 1
<211> LENGTH: 57
<212> TYPE: PRT
<213> ORGANISM: Dendroaspis angusticeps

<400> SEQUENCE: 1

Arg Pro Ser Phe Cys Asn Leu Pro Val Lys Pro Gly Pro Cys Asn Gly
1               5                   10                  15

Phe Phe Ser Ala Phe Tyr Tyr Ser Gln Lys Thr Asn Lys Cys His Ser
            20                  25                  30

Phe Thr Tyr Gly Gly Cys Lys Gly Asn Ala Asn Arg Phe Ser Thr Ile
        35                  40                  45

Glu Lys Cys Arg Arg Thr Cys Val Gly
    50                  55

<210> SEQ ID NO 2
<211> LENGTH: 57
<212> TYPE: PRT
<213> ORGANISM: Dendroaspis polylepis
```

<400> SEQUENCE: 2

Arg Pro Tyr Ala Cys Glu Leu Ile Val Ala Ala Gly Pro Cys Met Phe
1 5 10 15

Phe Ile Ser Ala Phe Tyr Tyr Ser Lys Gly Ala Asn Lys Cys Tyr Pro
20 25 30

Phe Thr Tyr Ser Gly Cys Arg Gly Asn Ala Asn Arg Phe Lys Thr Ile
35 40 45

Glu Glu Cys Arg Arg Thr Cys Val Val
50 55

<210> SEQ ID NO 3
<211> LENGTH: 57
<212> TYPE: PRT
<213> ORGANISM: Dendroaspis polylepis

<400> SEQUENCE: 3

Arg Pro Tyr Ala Cys Glu Leu Ile Val Ala Ala Gly Pro Cys Met Phe
1 5 10 15

Phe Ile Ser Ala Phe Tyr Tyr Ser Lys Gly Ser Asn Lys Cys Tyr Pro
20 25 30

Phe Thr Tyr Ser Gly Cys Arg Gly Asn Ala Asn Arg Phe Lys Thr Ile
35 40 45

Glu Glu Cys Arg Arg Thr Cys Val Val
50 55

<210> SEQ ID NO 4
<211> LENGTH: 83
<212> TYPE: PRT
<213> ORGANISM: Pseudechis australis

<400> SEQUENCE: 4

Met Ser Ser Gly Gly Leu Leu Leu Leu Leu Gly Leu Leu Thr Leu Trp
1 5 10 15

Glu Val Leu Thr Pro Val Ser Ser Lys Asp Arg Pro Arg Phe Cys Glu
20 25 30

Leu Pro Ala Asp Pro Gly Pro Cys Asn Gly Leu Phe Gln Ala Phe Tyr
35 40 45

Tyr Asn Pro Val Gln Arg Thr Cys Leu Lys Phe Arg Tyr Gly Gly Cys
50 55 60

Lys Gly Asn Pro Asn Thr Phe Lys Thr Ile Glu Glu Cys Lys Arg Thr
65 70 75 80

Cys Ala Ala

<210> SEQ ID NO 5
<211> LENGTH: 83
<212> TYPE: PRT
<213> ORGANISM: Pseudechis australis

<400> SEQUENCE: 5

Met Ser Ser Gly Gly Leu Leu Leu Leu Leu Gly Leu Leu Thr Leu Trp
1 5 10 15

Glu Val Leu Thr Pro Val Ser Ser Lys Asp Arg Pro Lys Phe Cys Glu
20 25 30

Leu Pro Ala Asp Pro Gly Pro Cys Asn Gly Leu Phe Gln Ala Phe Tyr
35 40 45

Tyr Asn Pro Val Gln Arg Lys Cys Leu Lys Phe Arg Tyr Gly Gly Cys
50 55 60

-continued

Lys Ala Asn Pro Asn Thr Phe Lys Thr Ile Glu Glu Cys Lys Arg Ile
65 70 75 80

Cys Ala Ala

<210> SEQ ID NO 6
<211> LENGTH: 59
<212> TYPE: PRT
<213> ORGANISM: Dendroaspis polylepis

<400> SEQUENCE: 6

Leu Gln His Arg Thr Phe Cys Lys Leu Pro Ala Glu Pro Gly Pro Cys
1 5 10 15

Lys Ala Ser Ile Pro Ala Phe Tyr Tyr Asn Trp Ala Ala Lys Lys Cys
20 25 30

Gln Leu Phe His Tyr Gly Gly Cys Lys Gly Asn Ala Asn Arg Phe Ser
35 40 45

Thr Ile Glu Lys Cys Arg His Ala Cys Val Gly
50 55

<210> SEQ ID NO 7
<211> LENGTH: 59
<212> TYPE: PRT
<213> ORGANISM: Dendroaspis polylepis

<400> SEQUENCE: 7

Leu Gln His Arg Thr Phe Cys Lys Leu Pro Ala Glu Pro Gly Pro Cys
1 5 10 15

Lys Ala Ser Ile Pro Ala Phe Tyr Tyr Asn Trp Ala Ala Lys Lys Cys
20 25 30

Gln Leu Phe His Tyr Gly Gly Cys Lys Gly Asn Ala Asn Arg Phe Ser
35 40 45

Thr Ile Glu Lys Cys Arg Arg Ala Cys Val Gly
50 55

<210> SEQ ID NO 8
<211> LENGTH: 79
<212> TYPE: PRT
<213> ORGANISM: Dendroaspis polylepis

<400> SEQUENCE: 8

Ser Gly His Leu Leu Leu Leu Leu Gly Leu Leu Thr Leu Trp Ala Glu
1 5 10 15

Leu Thr Pro Val Ser Gly Ala Ala Lys Tyr Cys Lys Leu Pro Leu Arg
20 25 30

Ile Gly Pro Cys Lys Arg Lys Ile Pro Ser Phe Tyr Tyr Lys Trp Lys
35 40 45

Ala Lys Gln Cys Leu Pro Phe Asp Tyr Ser Gly Cys Gly Gly Asn Ala
50 55 60

Asn Arg Phe Lys Thr Ile Glu Glu Cys Arg Arg Thr Cys Val Gly
65 70 75

<210> SEQ ID NO 9
<211> LENGTH: 59
<212> TYPE: PRT
<213> ORGANISM: Dendroaspis angusticeps

<400> SEQUENCE: 9

Gln Pro Arg Arg Lys Leu Cys Ile Leu His Arg Asn Pro Gly Arg Cys
1 5 10 15

```
Tyr Asp Lys Ile Pro Ala Phe Tyr Tyr Asn Gln Lys Lys Lys Gln Cys
            20                  25                  30

Glu Arg Phe Asp Trp Ser Gly Cys Gly Gly Asn Ser Asn Arg Phe Lys
        35                  40                  45

Thr Ile Glu Glu Cys Arg Arg Thr Cys Ile Gly
    50                  55


<210> SEQ ID NO 10
<211> LENGTH: 100
<212> TYPE: PRT
<213> ORGANISM: Bos taurus

<400> SEQUENCE: 10

Met Lys Met Ser Arg Leu Cys Leu Ser Val Ala Leu Leu Val Leu Leu
1               5                   10                  15

Gly Thr Leu Ala Ala Ser Thr Pro Gly Cys Asp Thr Ser Asn Gln Ala
            20                  25                  30

Lys Ala Gln Arg Pro Asp Phe Cys Leu Glu Pro Pro Tyr Thr Gly Pro
        35                  40                  45

Cys Lys Ala Arg Ile Ile Arg Tyr Phe Tyr Asn Ala Lys Ala Gly Leu
    50                  55                  60

Cys Gln Thr Phe Val Tyr Gly Gly Cys Arg Ala Lys Arg Asn Asn Phe
65                  70                  75                  80

Lys Ser Ala Glu Asp Cys Met Arg Thr Cys Gly Gly Ala Ile Gly Pro
                85                  90                  95

Trp Glu Asn Leu
            100


<210> SEQ ID NO 11
<211> LENGTH: 53
<212> TYPE: PRT
<213> ORGANISM: artificial sequence
<220> FEATURE:
<223> OTHER INFORMATION: synthetic polypeptide

<400> SEQUENCE: 11

Cys Asn Leu Pro Val Lys Pro Gly Pro Cys Asn Gly Phe Phe Ser Ala
1               5                   10                  15

Phe Tyr Tyr Ser Gln Lys Thr Asn Lys Cys His Ser Phe Thr Tyr Gly
            20                  25                  30

Gly Cys Lys Gly Asn Ala Asn Arg Phe Ser Thr Ile Glu Lys Cys Arg
        35                  40                  45

Arg Thr Cys Val Gly
    50


<210> SEQ ID NO 12
<211> LENGTH: 53
<212> TYPE: PRT
<213> ORGANISM: artificial sequence
<220> FEATURE:
<223> OTHER INFORMATION: synthetic polypeptide

<400> SEQUENCE: 12

Ser Phe Cys Asn Leu Pro Val Lys Pro Gly Pro Cys Asn Gly Phe Phe
1               5                   10                  15

Ser Ala Phe Tyr Tyr Ser Gln Lys Thr Asn Lys Cys His Ser Phe Thr
            20                  25                  30

Tyr Gly Gly Cys Lys Gly Asn Ala Asn Arg Phe Ser Thr Ile Glu Lys
        35                  40                  45
```

-continued

```
Cys Arg Arg Thr Cys
    50


<210> SEQ ID NO 13
<211> LENGTH: 51
<212> TYPE: PRT
<213> ORGANISM: artificial sequence
<220> FEATURE:
<223> OTHER INFORMATION: synthetic polypeptide

<400> SEQUENCE: 13

Cys Asn Leu Pro Val Lys Pro Gly Pro Cys Asn Gly Phe Phe Ser Ala
1               5                   10                  15

Phe Tyr Tyr Ser Gln Lys Thr Asn Lys Cys His Ser Phe Thr Tyr Gly
            20                  25                  30

Gly Cys Lys Gly Asn Ala Asn Arg Phe Ser Thr Ile Glu Lys Cys Arg
        35                  40                  45

Arg Thr Cys
    50


<210> SEQ ID NO 14
<211> LENGTH: 57
<212> TYPE: PRT
<213> ORGANISM: artificial sequence
<220> FEATURE:
<223> OTHER INFORMATION: synthetic polypeptide

<400> SEQUENCE: 14

Arg Pro Ser Phe Cys Asn Leu Pro Val Lys Pro Gly Pro Cys Lys Ala
1               5                   10                  15

Phe Phe Ser Ala Phe Tyr Tyr Ser Gln Lys Thr Asn Lys Cys His Ser
            20                  25                  30

Phe Thr Tyr Gly Gly Cys Lys Gly Asn Ala Asn Arg Phe Ser Thr Ile
        35                  40                  45

Glu Lys Cys Arg Arg Thr Cys Val Gly
    50                  55


<210> SEQ ID NO 15
<211> LENGTH: 57
<212> TYPE: PRT
<213> ORGANISM: artificial sequence
<220> FEATURE:
<223> OTHER INFORMATION: synthetic polypeptide

<400> SEQUENCE: 15

Arg Pro Lys Phe Cys Asn Leu Pro Val Lys Pro Gly Pro Cys Asn Gly
1               5                   10                  15

Phe Phe Ser Ala Phe Tyr Tyr Ser Gln Lys Thr Asn Lys Cys His Ser
            20                  25                  30

Phe Thr Tyr Gly Gly Cys Lys Gly Asn Ala Asn Arg Phe Ser Thr Ile
        35                  40                  45

Glu Lys Cys Arg Arg Thr Cys Val Gly
    50                  55


<210> SEQ ID NO 16
<211> LENGTH: 57
<212> TYPE: PRT
<213> ORGANISM: artificial sequence
<220> FEATURE:
<223> OTHER INFORMATION: synthetic polypeptide

<400> SEQUENCE: 16
```

-continued

```
Arg Pro Ser Phe Cys Asn Leu Pro Val Lys Pro Gly Pro Ser Asn Gly
1               5                   10                  15

Phe Phe Ser Ala Phe Tyr Tyr Ser Gln Lys Thr Asn Lys Cys His Ser
            20                  25                  30

Phe Thr Tyr Gly Gly Ser Lys Gly Asn Ala Asn Arg Phe Ser Thr Ile
        35                  40                  45

Glu Lys Cys Arg Arg Thr Cys Val Gly
    50                  55


<210> SEQ ID NO 17
<211> LENGTH: 60
<212> TYPE: PRT
<213> ORGANISM: Conus striatus

<400> SEQUENCE: 17

Lys Asp Arg Pro Ser Leu Cys Asp Leu Pro Ala Asp Ser Gly Ser Gly
1               5                   10                  15

Thr Lys Ala Glu Lys Arg Ile Tyr Tyr Asn Ser Ala Arg Lys Gln Cys
            20                  25                  30

Leu Arg Phe Asp Tyr Thr Gly Gln Gly Gly Asn Glu Asn Asn Phe Arg
        35                  40                  45

Arg Thr Tyr Asp Cys Gln Arg Thr Cys Leu Tyr Thr
    50                  55                  60
```